(12) United States Patent
Margolin et al.

(10) Patent No.: US 7,858,094 B2
(45) Date of Patent: Dec. 28, 2010

(54) TREM-1 SPLICE VARIANT FOR USE IN MODIFYING IMMUNE RESPONSES

(75) Inventors: Judith F. Margolin, Houston, TX (US); Marie-Claude Gingras, Houston, TX (US)

(73) Assignee: Geneprint Corporation, Houston, TX (US)

( * ) Notice: Subject to any disclaimer, the term of this patent is extended or adjusted under 35 U.S.C. 154(b) by 468 days.

(21) Appl. No.: 10/021,509

(22) Filed: Dec. 7, 2001

(65) Prior Publication Data

US 2002/0128444 A1 Sep. 12, 2002

Related U.S. Application Data

(60) Provisional application No. 60/254,404, filed on Dec. 8, 2000.

(51) Int. Cl.
*A61K 39/00* (2006.01)
*A61K 38/00* (2006.01)
*C07K 14/00* (2006.01)

(52) U.S. Cl. ............ 424/185.1; 530/300; 530/350
(58) Field of Classification Search ............ 424/185.1; 514/885
See application file for complete search history.

(56) References Cited

U.S. PATENT DOCUMENTS

| 6,087,331 A | 7/2000 | Newman et al. | |
|---|---|---|---|
| 6,420,526 B1 * | 7/2002 | Ruben et al. | 530/350 |
| 6,504,010 B1 * | 1/2003 | Wang et al. | 530/350 |

FOREIGN PATENT DOCUMENTS

| EP | 1 022 286 A1 | 7/2000 |
|---|---|---|
| WO | WO-9906557 | 2/1999 |
| WO | WO99/18126 | 4/1999 |

OTHER PUBLICATIONS

Feldman et al ., Transplant. Proc. 1998, 30, 4126-4127.*
Cochlovius et al ., Modern Drug Discovery, 2003, pp. 33-38.*
Van Noort et al. International Review of Cytology, 1998, vol. 178, pp. 127-204.*
Mikayama et al. PNAS, 1993. 90: 10056-10060.*
Burgess et al J Cell Biol. 111:2129-2138, 1990.*
Lazar et al. Mol Cell Biol. 8:1247-1252, 1988.*
Ngo et al, in the Protein Folding Problem and Tertiary Structure Prediction, 1994. (ed.), Birkhauser, Boston, MA, pp. 433 and 492-495.*
Dietrich, Jes, et al.; Cutting Edge: Signal-Regulatory Protein β1 is a DAP12-Associated Activating Receptor Expressed in Myeloid Cells; The Journal of Immunology, 2000, 164:9-12.
Lanier, Lewis L., et al.; Immunoreceptor DAP12 bearing a tyrosine-based activation motif is involved in activating NK cells; Nature, vol. 391, pp. 703-707, Feb. 12, 1998.
Bakker, Alexander B., et al.; Myeloid DAP1-associating lectin (MDL)-1 is a cell surface receptor involved in the activation of myeloid cells; Proc. Natl. Acad. Sci. USA, vol. 96, pp. 9792-9796, Aug. 1999 (Immunology).
Lanier, Lewis L.; NK Cell Receptors; Annu. Rev. Immunol. 1998, 16:359-93.
Tapping, Richard I., et al.; Soluble CD14-Mediated Cellular Responses to Lipopolysaccharide; Chem Immunol. Basel, Karger, 2000, vol. 74, pp. 108-121.
Campbell, Kerry S., et al.; DAP12: a key accessory protein for relaying signals by Natural Killer cell receptors; The International Journal of Biochemistry & Cell Biology 31 (1999) 631-636.
Bouchon, Axel, et al.; Cutting Edge: Inflammatory Responses Can Be Triggered by TREM-1, a Novel Receptor Expressed on Neutrophils and Monocytes; The Journal of Immunology, 2000, 164: 4991-4995.
Lanier, Lewis L., et al.; Association of DAP12 with Activating CD94/NKG2C NK Cell Receptors; Immunity, vol. 8, pp. 693-701, Jun. 1998.
European Search Report Application No. 01994219.
Lanier et al, "The IT AM-bearing transmembrane adator DAP 12 in lymphoid and myeloid cell function," Immunology Today: Viewpoint vol. 21 No. 12, Dec. 2000, pp. 611-614.
Dietrich et al, "Human inhibitory and activating Ig-like receptors which modulate the function of myeloid cells," Microbes and Infection 2000, pp. 323-329.
Bouchan et al, "TREM-1 amplifies inflammation and is a criucial mediator of septic shock," Nature vol. 410, Apr. 26, 2001, pp. 1103-1107.
Nochi et al, "Modulation of Hepatic Granulomatous Responses by Transgene Expression of DAP 12 or TREM-1-Ig Molecules," American Journal of Pathology vol. 162, No. 4, Apr. 2003, pp. 1191-1201.
Wilson et al, "DAP 12 and KAP10 (DAP10)-Novel Transmembrane Adaptor Proteins of the CD3 Family," Immunologic Research 22/1, 2000, pp. 21-42.
Marie-Claude Gingras, Helene Lapillonne, Judith F. Margolin. TREM-1, MDL-1, and DAP12 expression is associated with a mature stage of myeloid development. Molecular Immunology vol. 38 pp. 817-824, 2001.
Phillipp Haselmeyer, Ludger Grosse-Hovest, Philipp Von Landerberg, Hansjorg Schild, and Markus P. Radsak. TREM-1 ligand expression on platelets enhances neutrophil activation. Blood, vol. 110, pp. 1029-1035, 2007.

* cited by examiner

*Primary Examiner*—Michail A Belyavskyi

(57) ABSTRACT

The present invention relates to a soluble receptor variant of TREM-1. More particularly, present invention relates to methods of modulating an immune response by administering variants of TREM-1.

9 Claims, 5 Drawing Sheets

```
                          attgtggtgccttgtagctgtcccgggagccctcagcagcagttggagctggtgcacaggaagg      64

ATGAGGAAGACCAGGCTCTGGGGGCTGCTGTGGATGCTCTTTGTCTCAGAACTCCGAGCTGCAACTAAATTAACTGAGGAAAAG   148
 M  R  K  T  r  l  w  g  l  l  w  m  l  f  v  s  E  L  R  A  A  T  K  L  T  E  E  K    28
 M  R  K  T  r  l  w  g  l  l  w  m  l  f  v  s  E  L  R  A  A  T  K  L  T  E  E  K    28

TATGAACTGAAAGAGGGCAGACCCTGGATGTGAAATGTGACTACACGCTAGAGAAGTTTGCCAGCAGCCAGAAAGCTTGGCAG    232
 Y  E  L  K  E  G  Q  T │L  D  V  K  C  D  Y│ T  L  E  K  F  A  S  S  Q  K  A  W  Q    56
 Y  E  L  K  E  G  Q  T │L  D  V  K  C  D  Y│ T  L  E  K  F  A  S  S  Q  K  A  W  Q    56

ATAATAAGGGACGGAGAGATGCCCAAGACCCTGGCATGCACAGAGAGGCCTTCAAAGAATTCCCATCCAGTCCAAGTCGGGAGG  316
 I  I  R  D  G  E  M  P  K  T  L  A  C  T  E  R  P  S  K  N  S  H  P  V  Q  V  G  R    84
 I  I  R  D  G  E  M  P  K  T  L  A  C  T  E  R  P  S  K  N  S  H  P  V  Q  V  G  R    84

ATCATACTAGAAGACTACCATGATCATGGTTTACTGCGCGTCCGAATGGTCAACCTTCAAGTGGAAGATTCTGGACTGTATCAG  400
 I  I  L  E  D  Y  H  D  H  G  L  L  R  V  R  M  V  N  L  Q  V  E │D  S  G  L  Y  Q   112
 I  I  L  E  D  Y  H  D  H  G  L  L  R  V  R  M  V  N  L  Q  V  E │D  S  G  L  Y  Q   112

TGTGTGATCTACCAGCCTCCCAAGGAGCCTCACATGCTGTTCGATCGCATCCGCTTGGTGGTGACCAAGGGTTTTTCAGGGACC   484
│C│ V  I  Y  Q  P  P  K  E  P  H  M  L  F  D  R  I  R  L  V  V  T  K  G  F  S  G  T   140
│C│ V  I  Y  Q  P  P  K  E  P  H  M  L  F  D  R  I  R  L  V  V  T  K  -  -  -  -  -   136

CCTGGCTCCAATGAGAATTCTACCCAGAATGTGTATAAGATTCCTCCTACCACCACTAAGGCCTTGTGCCCACTCTATACCAGC    568
 P  G  S  N  E  N+ S  T  Q  N  V  Y  K  I  P  P  T  T  T  K  A  L  C  P  L  Y  T  S   168
 -  -  -  -  -  -  -  -  -  -  -  -  -  -  -  -  -  -  -  -  -  -  -  -  -  -  -  -   136

CCCAGAACTGTGACCCAAGCTCCACCCAAGTCAACTGCCGATGTCTCCACTCCTGACTCTGAAATCAACCTTACAAATGTGACA    652
 P  R  T  V  T  Q  A  P  P  K  S  T  A  D  V  S  T  P  D  S  E  I  N+ L  T  N+ V  T   196
 -  -  -  -  -  -  -  -  -  -  -  -  -  -  -  -  -  -  -  -  -  -  -  -  -  -  -  -   136

GATATCATCAGGGTTCCGGTGTTCAACATTGTCATTCTCCTGGCTGGTGGATTCCTGAGTAAGAGCCTGGTCTTCTCTGTCCTG   736
 D  I  I  R │V  P  V  F  N  I  V  I  L  L  A  G  G  F  L  S  K  S  L  V  F  S  V  L   224
 -  -  -  - -G  F  R  C  S  T  L  S  F  S  W  L  V  D  S  *                           150

TTTGCTGTCACGCTGAGGTCATTTGTACCCTAGcccacgaacccacgagaatgtcctctgacttccagccacatccatctggc    820
 F  A  V  T  L │R  S  F  V  P  *                                                      234 agttgtgccaagggaggagggaggaggtaaaaggcagggagttaataacatgaattaaatctgtaatcaccagctatttctaaa   904
gtcagcgtctcaccttaaaaaaaaaaaaaaaaaaaaaaaaaaaaa                                          948
```

FIGURE 4

SEQUENCE LISTING

<160> NUMBER OF SEQ ID NOS: 28

<210> SEQ ID NO 1
<211> LENGTH: 755
<212> TYPE: DNA
<213> ORGANISM: HUMAN

<400> SEQUENCE: 1

```
attgtggtgc cttgtagctg tcccgggagc cctcagcagc agttggagct ggtgcacagg      60
aaggatgagg aagaccaggc tctgggggct gctgtggatg ctctttgtct cagaactccg     120
agctgcaact aaattaactg aggaaaagta tgaactgaaa gaggggcaga ccctggatgt     180
gaaatgtgac tacacgctag agaagtttgc cagcagccag aaagcttggc agataataag     240
ggacggagag atgcccaaga ccctggcatg cacagagagg ccttcaaaga attcccatcc     300
agtccaagtg gggaggatca tactagaaga ctaccatgat catggtttac tgcgcgtccg     360
aatggtcaac cttcaagtgg aagattctgg actgtatcag tgtgtgatct accagcctcc     420
caaggagcct cacatgctgt tcgatcgcat ccgcttggtg gtgaccaagg ggttccggtg     480
ttcaacattg tcattctcct ggctggtgga ttcctgagta agagcctggt cttctctgtc     540
ctgtttgctg tcacgctgag gtcatttgta ccctaggccc acgaacccac gagaatgtcc     600
tctgacttcc agccacatcc atctggcagt tgtgccaagg gaggagggag gaggtaaaag     660
gcagggagtt aataacatga attaaatctg taatcaccag ctatttctaa agtcagcgtc     720
tcaccttaaa aaaaaaaaaa aaaaaaaaaa aaaaa                                755
```

<210> SEQ ID NO 2
<211> LENGTH: 150
<212> TYPE: PRT
<213> ORGANISM: HUMAN

<400> SEQUENCE: 2

```
Met Arg Lys Thr Arg Leu Trp Gly Leu Leu Trp Met Leu Phe Val Ser
1               5                   10                  15

Glu Leu Arg Ala Ala Thr Lys Leu Thr Glu Glu Lys Tyr Glu Leu Lys
            20                  25                  30

Glu Gly Gln Thr Leu Asp Val Lys Cys Asp Tyr Thr Leu Glu Lys Phe
        35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Arg Cys Ser Thr Leu Ser Phe
    130                 135                 140

Ser Trp Leu Val Asp Ser
145                 150
```

<210> SEQ ID NO 3
<211> LENGTH: 1023

```
<212> TYPE: DNA
<213> ORGANISM: MUS MUSCULUS

<400> SEQUENCE: 3
ttcaagggaa aagcaagatc ttgcacaagg tccccctccgg ctggctgctg gcaaaggaaa        60
ggtgccatgg gacctctcca ccagtttctc ctgctgctga tcacagccct gtcccaagcc       120
ctcaacacca cggtgctgca gggcatggcc ggccagtcct tgagggtgtc atgtacttat       180
gacgccttga agcactgggg gagacgcaag gcctggtgtc ggcagctggg tgaggagggc       240
ccatgccagc gtgtggtgag cacacacggt gtgtgggctg ctggccttcc tgaagaagcg       300
gatgggagca cagtcatcgc agatgacacc cttgctggaa ccgtcaccat cactctgaag       360
aacctccaag ccggtgacgc gggcctctac cagtgtcaga gtctccgagg ccgagagcgt       420
gaggtcctgc agaaagtact ggtggaggtg ctggaggacc tctagatga ccaagatgct        480
ggagatctct gggtccccga ggagtcatcg agtttcgagg gtgcccaagt ggaacacagc       540
acctccagga atcaagagac ctccttccca cccacctcca ttcttctcct cctggcctgc       600
gttctcctga gcaagtttct tgcagccagc atcctctggg ctgtggccag ggcaggcag        660
aagccgggaa cacctgtggt cagagggctg gactgtggcc aagatgctgg gcaccaactt       720
cagatcctca ctggacccgg aggtacgtga gagaattctg agtggggagga gaactacagc      780
ttaagtccag ccaggagtca atccagcctg catgctctcc cctcctccac caagacttct       840
gtttctgcta cttttgcttc agaggccgcc tctgccttca gccacctatc ctgggaacag       900
gaatactgtg tgtacatctg tggtgagttg ggaagaacac tggatgggtg tccgtaaaat       960
tctggaattt gggaattaac atcctcccac accagaaaat agaaaaaaaa gaaccatggg      1020
gcc                                                                    1023

<210> SEQ ID NO 4
<211> LENGTH: 995
<212> TYPE: DNA
<213> ORGANISM: MUS MUSCULUS

<400> SEQUENCE: 4
acttgccttg gggccattgg cagttagcac accaggaagg agcttcatac agaggaggca        60
gggacctggg ggatgtcacc gctgctgcta tggctgggc tgatgctctg tgtctcggga       120
ctccaagctg gagatgagga agaacacaag tgttttctgg agggcgagaa cctgacccctg      180
acttgtcctt acaacatcat gctatactca ctgagcctga aggcctggca gcgggtcaga       240
agccacggtt ctccagagac tctggtgctc acaaacacca gaaaggcaga cttcaacgtg       300
gccagggctg ggaagtactt gctggaggat tatcccaccg aatctgtcgt caaggtcacg       360
gtgactgggc tgcagaggca agatgtgggg ctgtaccagt gtgtggtcta cctctctcct       420
gacaatgtta tcattctgcg tcaacggata cggctggcat ggtgtcaagg gaagccagtg       480
atggtgatcg ttctgacgtg tggcttcata ctaaacaagg gcctggtctt tcagtcctg       540
tttgtctttc tctgcaaagc tgggcctaag gtgttacagc cttccaagac atccaaagta       600
cagggagtct ctgagaaaca gtagccttcc tgctacaagc tgtgagcaca ccttcccctta      660
tctattaaca acataccaga tgttctgtat tggggacaat ctgggccttc ctacattctc       720
cttgtgaact ctagttagca catgatactc ccagaggaca gctctgagga gagctgtgta       780
gaaggaggct catgagacat cagtgaagaa tataaaattg agagagattt ggacctttgg       840
tggagcagtt aagcaggacc cacagagaat tcacctcaaa atcttatcac catttctctc       900
```

| | |
|---|---|
| ctgctaacca ggtctgccat gctgtggact ggtaaaacct atatgatgta acctatctct | 960 |
| cttctgataa taataaaaaa aattgtattt ttttc | 995 |

<210> SEQ ID NO 5
<211> LENGTH: 990
<212> TYPE: DNA
<213> ORGANISM: MUS MUSCULUS

<400> SEQUENCE: 5

| | |
|---|---|
| gagcttgaag gatgaggaag gctgggctct ggggactgct gtgcgtgttc tttgtctcag | 60 |
| aagtcaaagc tgccattgtt ctagaggaag aaaggtatga cctagtggag ggccagactt | 120 |
| tgacagtgaa gtgtcccttc aacatcatga agtatgccaa cagccagaag gcttggcaga | 180 |
| gactaccaga cgggaaggaa cccttgaccc tggtggtcac acagaggccc tttacaagac | 240 |
| ccagtgaagt ccacatgggg aagttcaccc tgaaacatga ccctagtgag gccatgctac | 300 |
| aagttcaaat gactgacctt caagtgacag actctggatt gtatcgttgt gtgatttacc | 360 |
| atcctccgaa tgaccctgtt gtgctcttcc atcctgtccg cctggtggtg accaagggtt | 420 |
| cttcagatgt gttcactcct gtcatcattc ctattacaag gctgacagag cgtcccatcc | 480 |
| ttattaccac aaaatactca cccagtgaca caactacaac ccgatcccta cccaagccca | 540 |
| ctgcggttgt ttcctctcct ggtcttggag tcactatcat aaatgggaca gatgctgaca | 600 |
| gtgtctccac atccagtgtt actatttcag tcatctgtgg acttctcagc aagagcctgg | 660 |
| ttttcatcat cttattcatt gtcacaaaga ggacatttgg atgacagaac ttgaagctat | 720 |
| acaatagtga ccttcagcgg tgtctatttc acaggaggag ctgaggtggt ggggctgagg | 780 |
| aggagctatg acatgaattg aacctgtaat caccggtgac gtctaaggct caggatatcc | 840 |
| tcagctgacc ctgtccactc tcctcatttt atccatcatc ttggggatgt gctctgcacc | 900 |
| cttagaaaag gggaaaccat tcccagaaca ctctggccat tccccctaaa tagttgggtt | 960 |
| ggcctgaaat aaagagaaac tccagagctt | 990 |

<210> SEQ ID NO 6
<211> LENGTH: 1041
<212> TYPE: DNA
<213> ORGANISM: MUS MUSCULUS

<400> SEQUENCE: 6

| | |
|---|---|
| tgacatgcct gatcctctct tttctgcagt tcaagggaaa gacgagatct tgcacaaggc | 60 |
| actctgcttc tgcccttggc tggggaaggg tggcatggag cctctccggc tgctcatctt | 120 |
| actctttgtc acagagctgt ccggagccca caacaccaca gtgttccagg gcgtggcggg | 180 |
| ccagtccctg caggtgtctt gcccctatga ctccatgaag cactggggga ggcgcaaggc | 240 |
| ctggtgccgc cagctgggag agaagggccc atgccagcgt gtggtcagca cgcacaactt | 300 |
| gtggctgctg tccttcctga ggaggtgaaa tgggagcaca gccatcacag acgatacct | 360 |
| gggtggcact ctcaccatta cgctgcggaa tctacaaccc catgatgcgg gtctctacca | 420 |
| gtgccagagc ctccatggca gtgaggctga caccctcagg aaggtcctgg tggaggtgct | 480 |
| ggcagacccc ctggatcacc gggatgctgg agatctctgg ttccccgggg agtctgagag | 540 |
| cttcgaggat gccatgtgg agcacagcat tccaggagc ctcttggaag agaaatcccc | 600 |
| cttcccaccc acttccatcc ttctcctcct ggcctgcatc tttctcatca agattctagc | 660 |
| agccagcgcc ctctgggctg cagcctggca tggacagaag ccaggacac atccacccag | 720 |
| tgaactggac tgtggccatg acccagggta tcagctccaa actctgccag ggctgagaga | 780 |

```
cacgtgaagg aagatgatgg gaggaaaagc ccaggagaag tcccaccagg gaccagccca    840
gcctgcatac ttgccacttg gccaccagga ctccttgttc tgctctggca agagactact    900
ctgcctgaac actgcttctc ctggaccctg gaagcaggga ctggttgagg gagtggggag    960
gtggtaagaa cacctgacaa cttctgaata ttggacattt taaacactta caaataaatc   1020
caagactgtc atatttaaaa a                                              1041

<210> SEQ ID NO 7
<211> LENGTH: 884
<212> TYPE: DNA
<213> ORGANISM: HUMAN

<400> SEQUENCE: 7
ctactactac taaattcgcg gccggtcgac gctggtgcac aggaaggatg aggaagacca     60
ggctctgggg gctgctgtgg atgctctttg tctcagaact ccgagctgca actaaattaa    120
ctgaggaaaa gtatgaactg aaagaggggc agaccctgga tgtgaaatgt gactacacgc    180
tagagaagtt tgccagcagc cagaaagctt ggcagataat aagggacgga gagatgccca    240
agaccctggc atgcacagag aggccttcaa agaattccca tccagtccaa gtggggagga    300
tcatactaga agactaccat gatcatggtt tactgcgcgt ccgaatggtc aaccttcaag    360
tggaagattc tggactgtat cagtgtgtga tctaccagcc tcccaaggag cctcacatgc    420
tgttcgatcg catccgcttg gtggtgacca agggtttttc agggacccct ggctccaatg    480
agaattctac ccagaatgtg tataagattc tcctaccac cactaaggcc ttgtgcccac    540
tctataccag ccccagaact gtgacccaag ctccacccaa gtcaactgcc gatgtctcca    600
ctcctgactc tgaaatcaac cttacaaatg tgacagatat catcagggtt ccggtgttca    660
acattgtcat tctcctggct ggtggattcc tgagtaagag cctggtcttc tctgtcctgt    720
ttgctgtcac gctgaggtca tttgtaccct aggcccacga acccacgaga atgtcctctg    780
acttccagcc acatccatct ggcagttgtg ccaagggagg agggaggagg taaaaggcag    840
ggagttaata acatgaatta aatctgtaat caccagctat ttct                     884

<210> SEQ ID NO 8
<211> LENGTH: 948
<212> TYPE: DNA
<213> ORGANISM: HUMAN

<400> SEQUENCE: 8
attgtggtgc cttgtagctg tcccgggagc cctcagcagc agttggagct ggtgcacagg     60
aaggatgagg aagaccaggc tctgggggct gctgtggatg ctctttgtct cagaactccg    120
agctgcaact aaattaactg aggaaaagta tgaactgaaa gaggggcaga ccctggatgt    180
gaaatgtgac tacacgctag agaagtttgc cagcagccag aaagcttggc agataataag    240
ggacggagag atgcccaaga ccctggcatg cacagagagg ccttcaaaga attcccatcc    300
agtccaagtg gggaggatca tactagaaga ctaccatgat catggtttac tgcgcgtccg    360
aatggtcaac cttcaagtgg aagattctgg actgtatcag tgtgtgatct accagcctcc    420
caaggagcct cacatgctgt tcgatcgcat ccgcttggtg gtgaccaagg gttttttcagg   480 gacccctggc tccaatgaga attctaccca gaatgtgtat aagattcctc ctaccaccac    540
taaggccttg tgcccactct ataccagccc cagaactgtg acccaagctc acccaagtc    600 aactgccgat gtctccactc ctgactctga aatcaacctt acaaatgtga cagatatcat    660
```

-continued

```
cagggttccg gtgttcaaca ttgtcattct cctggctggt ggattcctga gtaagagcct    720
ggtcttctct gtcctgtttg ctgtcacgct gaggtcattt gtaccctagg cccacgaacc    780
cacgagaatg tcctctgact tccagccaca tccatctggc agttgtgcca agggaggagg    840
gaggaggtaa aaggcaggga gttaataaca tgaattaaat ctgtaatcac cagctatttc    900
taaagtcagc gtctcacctt aaaaaaaaaa aaaaaaaaa aaaaaaa                    948
```

<210> SEQ ID NO 9
<211> LENGTH: 884
<212> TYPE: DNA
<213> ORGANISM: HUMAN

<400> SEQUENCE: 9

```
ctactactac taaattcgcg gccggtcgac gctggtgcac aggaaggatg aggaagacca     60
ggctctgggg gctgctgtgg atgctctttg tctcagaact ccgagctgca actaaattaa   120
ctgaggaaaa gtatgaactg aaagaggggc agaccctgga tgtgaaatgt gactacacgc   180
tagagaagtt tgccagcagc cagaaagctt ggcagataat aagggacgga gagatgccca   240
agaccctggc atgcacagag aggccttcaa agaattccca tccagtccaa gtggggagga   300
tcatactaga agactaccat gatcatggtt tactgcgcgt ccgaatggtc aaccttcaag   360
tggaagattc tggactgtat cagtgtgtga tctaccagcc tcccaaggag cctcacatgc   420
tgttcgatcg catccgcttg gtggtgacca agggttttc agggacccct ggctccaatg   480
agaattctac ccagaatgtg tataagattc ctcctaccac cactaaggcc ttgtgcccac   540
tctataccag ccccagaact gtgacccaag ctccacccaa gtcaactgcc gatgtctcca   600
ctcctgactc tgaaatcaac cttacaaatg tgacagatat catcagggtt ccggtgttca   660
acattgtcat tctcctggct ggtggattcc tgagtaagag cctggtcttc tctgtcctgt   720
ttgctgtcac gctgaggtca tttgtaccct aggcccacga acccacgaga atgtcctctg   780
acttccagcc acatccatct ggcagttgtg ccaagggagg agggaggagg taaaaggcag   840
ggagttaata acatgaatta aatctgtaat caccagctat ttct                     884
```

<210> SEQ ID NO 10
<211> LENGTH: 1023
<212> TYPE: DNA
<213> ORGANISM: HUMAN

<400> SEQUENCE: 10

```
ttcaagggaa aagcaagatc ttgcacaagg tccctccgg ctggctgctg gcaaggaaa      60 ggtgccatgg gacctctcca ccagtttctc ctgctgctga tcacagccct gtcccaagcc   120
ctcaacacca cggtgctgca gggcatggcc ggccagtcct tgagggtgtc atgtacttat   180
gacgccttga agcactgggg gagacgcaag gcctggtgtc ggcagctggg tgaggagggc   240
ccatgccagc gtgtggtgag cacacacggt gtgtgggctg ctggccttcc tgaagaagcg   300
gatgggagca cagtcatcgc agatgacacc cttgctggaa ccgtcaccat cactctgaag   360
aacctccaag ccggtgacgc gggcctctac cagtgtcaga gtctccgagg ccgagagcgt   420
gaggtcctgc agaaagtact ggtggaggtg ctggaggacc tctagatga ccaagatgct    480 ggagatctct gggtccccga ggagtcatcg agtttcgagg gtgcccaagt ggaacacagc   540
acctccagga atcaagagac ctccttccca cccacctcca ttcttctcct cctggcctgc   600
gttctcctga gcaagtttct tgcagccagc atcctctggg ctgtggccag ggcaggcag    660 aagccgggaa cacctgtggt cagagggctg gactgtggcc aagatgctgg gcaccaactt   720
```

-continued

```
cagatcctca ctggacccgg aggtacgtga gagaattctg agtgggagga gaactacagc      780
ttaagtccag ccaggagtca atccagcctg catgctctcc cctcctccac caagacttct      840
gtttctgcta cttttgcttc agaggccgcc tctgccttca gccacctatc ctgggaacag      900
gaatactgtg tgtacatctg tggtgagttg ggaagaacac tggatgggtg tccgtaaaat      960
tctggaattt gggaattaac atcctcccac accagaaaat agaaaaaaaa gaaccatggg     1020
gcc                                                                   1023
```

<210> SEQ ID NO 11
<211> LENGTH: 1041
<212> TYPE: DNA
<213> ORGANISM: HUMAN

<400> SEQUENCE: 11

```
tgacatgcct gatcctctct tttctgcagt tcaagggaaa gacgagatct tgcacaaggc       60
actctgcttc tgcccttggc tggggaaggg tggcatggag cctctccggc tgctcatctt      120
actctttgtc acagagctgt ccggagccca caacaccaca gtgttccagg cgtggcggg      180 ccagtccctg caggtgtctt gcccctatga ctccatgaag cactggggga ggcgcaaggc      240
ctggtgccgc cagctgggag agaagggccc atgccagcgt gtggtcagca cgcacaactt      300
gtggctgctg tccttcctga ggaggtggaa tgggagcaca gccatcacag acgataccct      360
gggtggcact ctcaccatta cgctgcggaa tctacaaccc catgatgcgg gtctctacca      420
gtgccagagc ctccatggca gtgaggctga caccctcagg aaggtcctgg tggaggtgct      480
ggcagacccc ctggatcacc gggatgctgg agatctctgg ttccccgggg agtctgagag      540
cttcgaggat gccatgtgg agcacagcat tccaggagc ctcttggaag agaaatccc       600 cttcccaccc acttccatcc ttctcctcct ggcctgcatc tttctcatca agattctagc      660
agccagcgcc ctctgggctg cagcctgca tggacagaag ccaggacac atccacccag      720 tgaactggac tgtggccatg acccagggta tcagctccaa actctgccag ggctgagaga      780
cacgtgaagg aagatgatgg gaggaaaagc ccaggagaag tcccaccagg gaccagccca      840
gcctgcatac ttgccacttg gccaccagga ctccttgttc tgctctggca agagactact      900
ctgcctgaac actgcttctc ctggaccctg gaagcaggga ctggttgagg gagtggggag      960
gtggtaagaa cacctgacaa cttctgaata ttggacattt taaacactta caaataaatc     1020
caagactgtc atatttaaaa a                                              1041
```

<210> SEQ ID NO 12
<211> LENGTH: 995
<212> TYPE: DNA
<213> ORGANISM: MUS MUSCULUS

<400> SEQUENCE: 12

```
acttgccttg gggccattgg cagttagcac accaggaagg agcttcatac agaggaggca       60
gggacctggg ggatgtcacc gctgctgcta tggctggggc tgatgctctg tgtctcggga      120
ctccaagctg gagatgagga agaacacaag tgttttctgg agggcgagaa cctgaccctg      180
acttgtcctt acaacatcat gctatactca ctgagcctga aggcctggca gcgggtcaga      240
agccacggtt ctccagagac tctggtgctc acaaacacca gaaaggcaga cttcaacgtg      300
gccagggctg ggaagtactt gctgaggat tatcccaccg aatctgtcgt caaggtcacg      360
gtgactgggc tgcagaggca agatgtgggg ctgtaccagt gtgtggtcta cctctctcct      420
```

```
gacaatgtta tcattctgcg tcaacggata cggctggcat ggtgtcaagg gaagccagtg      480
atggtgatcg ttctgacgtg tggcttcata ctaaacaagg gcctggtctt ctcagtcctg      540
tttgtctttc tctgcaaagc tgggcctaag gtgttacagc cttccaagac atccaaagta      600
cagggagtct ctgagaaaca gtagccttcc tgctacaagc tgtgagcaca ccttccctta      660
tctattaaca acataccaga tgttctgtat tggggacaat ctgggccttc ctacattctc      720
cttgtgaact ctagttagca catgatactc ccagaggaca gctctgagga gagctgtgta      780
gaaggaggct catgagacat cagtgaagaa tataaaattg agagagattt ggacctttgg      840
tggagcagtt aagcaggacc cacagagaat tcacctcaaa atcttatcac catttctctc      900
ctgctaacca ggtctgccat gctgtggact ggtaaaacct atatgatgta acctatctct      960
cttctgataa taataaaaaa aattgtattt ttttc                                 995

<210> SEQ ID NO 13
<211> LENGTH: 990
<212> TYPE: DNA
<213> ORGANISM: MUS MUSCULUS

<400> SEQUENCE: 13
gagcttgaag gatgaggaag gctgggctct ggggactgct gtgcgtgttc tttgtctcag       60
aagtcaaagc tgccattgtt ctagaggaag aaaggtatga cctagtggag ggccagactt      120
tgacagtgaa gtgtcccttc aacatcatga agtatgccaa cagccagaag gcttggcaga      180
gactaccaga cgggaaggaa cccttgaccc tggtggtcac acagaggccc tttacaagac      240
ccagtgaagt ccacatgggg aagttcaccc tgaaacatga ccctagtgag gccatgctac      300
aagttcaaat gactgacctt caagtgacag actctggatt gtatcgttgt gtgatttacc      360
atcctccgaa tgaccctgtt gtgctcttcc atcctgtccg cctggtggtg accaagggtt      420
cttcagatgt gttcactcct gtcatcattc ctattacaag gctgacagag cgtcccatcc      480
ttattaccac aaaatactca cccagtgaca caactacaac ccgatcccta cccaagccca      540
ctgcggttgt ttcctctcct ggtcttggag tcactatcat aaatgggaca gatgctgaca      600
gtgtctccac atccagtgtt actatttcag tcatctgtgg acttctcagc aagagcctgg      660
ttttcatcat cttattcatt gtcacaaaga ggacatttgg atgacagaac ttgaagctat      720
acaatagtga ccttcagcgg tgtctatttc acaggaggag ctgaggtggt ggggctgagg      780
aggagctatg acatgaattg aacctgtaat caccggtgac gtctaaggct caggatatcc      840
tcagctgacc ctgtccactc tcctcatttt atccatcatc ttggggatgt gctctgcacc      900
cttagaaaag gggaaaccat tcccagaaca ctctggccat tcccctaaa tagttgggtt       960 ggcctgaaat aaagagaaac tccagagctt                                       990

<210> SEQ ID NO 14
<211> LENGTH: 22
<212> TYPE: DNA
<213> ORGANISM: HUMAN

<400> SEQUENCE: 14
ggacggagag atgcccaaga cc                                                22

<210> SEQ ID NO 15
<211> LENGTH: 22
<212> TYPE: DNA
<213> ORGANISM: HUMAN

<400> SEQUENCE: 15
```
accagccagg agaatgacaa tg                                       22

<210> SEQ ID NO 16
<211> LENGTH: 20
<212> TYPE: DNA
<213> ORGANISM: HUMAN

<400> SEQUENCE: 16
cagagaggcc ttcaaagaat                                          20

<210> SEQ ID NO 17
<211> LENGTH: 17
<212> TYPE: DNA
<213> ORGANISM: HUMAN

<400> SEQUENCE: 17
cctcccttgg cacaact                                             17

<210> SEQ ID NO 18
<211> LENGTH: 22
<212> TYPE: DNA
<213> ORGANISM: HUMAN

<400> SEQUENCE: 18
ttgtggagga tttgaagttg ag                                       22

<210> SEQ ID NO 19
<211> LENGTH: 22
<212> TYPE: DNA
<213> ORGANISM: HUMAN

<400> SEQUENCE: 19
cgtgagtcta agggttggat gg                                       22

<210> SEQ ID NO 20
<211> LENGTH: 20
<212> TYPE: DNA
<213> ORGANISM: HUMAN

<400> SEQUENCE: 20
atcccaccgg cccttacact                                          20

<210> SEQ ID NO 21
<211> LENGTH: 19
<212> TYPE: DNA
<213> ORGANISM: HUMAN

<400> SEQUENCE: 21
ggggagcggt ctggtctct                                           19

<210> SEQ ID NO 22
<211> LENGTH: 20
<212> TYPE: DNA
<213> ORGANISM: HUMAN

<400> SEQUENCE: 22
ggagccctca gcagcagttg                                          20

<210> SEQ ID NO 23
<211> LENGTH: 20
<212> TYPE: DNA
<213> ORGANISM: HUMAN

<210> SEQ ID NO 24
<211> LENGTH: 20
<212> TYPE: DNA
<213> ORGANISM: HUMAN

<400> SEQUENCE: 24
tttaaggtga gacgctgact                                                 20

<210> SEQ ID NO 25
<211> LENGTH: 19
<212> TYPE: DNA
<213> ORGANISM: HUMAN

<400> SEQUENCE: 25
cgaatggtca accttcaag                                                  19

<210> SEQ ID NO 26
<211> LENGTH: 20
<212> TYPE: DNA
<213> ORGANISM: HUMAN

<400> SEQUENCE: 26
ctggtataga gtgggcacaa                                                 20

<210> SEQ ID NO 27
<211> LENGTH: 22
<212> TYPE: DNA
<213> ORGANISM: HUMAN

<400> SEQUENCE: 27
aagctccacc caagtcaact gc                                              22

<210> SEQ ID NO 28
<211> LENGTH: 234
<212> TYPE: PRT
<213> ORGANISM: HUMAN

<400> SEQUENCE: 28

Met Arg Lys Thr Arg Leu Trp Gly Leu Leu Trp Met Leu Phe Val Ser
1               5                   10                  15

Glu Leu Arg Ala Ala Thr Lys Leu Thr Glu Glu Lys Tyr Glu Leu Lys
                20                  25                  30

Glu Gly Gln Thr Leu Asp Val Lys Cys Asp Tyr Thr Leu Glu Lys Phe
            35                  40                  45

Ala Ser Ser Gln Lys Ala Trp Gln Ile Ile Arg Asp Gly Glu Met Pro
        50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
                100                 105                 110

Cys Val Ile Tyr Gln Pro Pro Lys Glu Pro His Met Leu Phe Asp Arg
            115                 120                 125

Ile Arg Leu Val Val Thr Lys Gly Phe Ser Gly Thr Pro Gly Ser Asn
    130                 135                 140

<210> SEQ ID NO 23 ttgggtggag cttgggtcac                                                 20

-continued

```
Glu Asn Ser Thr Gln Asn Val Tyr Lys Ile Pro Pro Thr Thr Thr Lys
145                 150                 155                 160

Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
            180                 185                 190

Thr Asn Val Thr Asp Ile Ile Arg Val Pro Val Phe Asn Ile Val Ile
        195                 200                 205

Leu Leu Ala Gly Gly Phe Leu Ser Lys Ser Leu Val Phe Ser Val Leu
        210                 215                 220

Phe Ala Val Thr Leu Arg Ser Phe Val Pro
225                 230
```

TREM-1 SPLICE VARIANT FOR USE IN MODIFYING IMMUNE RESPONSES

This application claims priority to U.S. Provisional Application No. 60/254,404, which was filed on Dec. 8, 2000.

This invention was made with government support under Grant No. CA80200 awarded by the National Institutes of Health. The United States Government may have certain rights in the invention.

FIELD OF THE INVENTION

The present invention relates to the field of immunology. More particularly, the present invention relates to inflammation and modulating the role of myeloid cell activation and the inflammatory response.

DESCRIPTION OF THE RELATED ART

Inflammation is a cellular and vascular response to injury, which includes release of inflammatory mediators, vasodilation, exudation of plasma and migration of inflammatory cells to the injury site. The cellular and vascular responses result in the classical clinical symptoms of swelling, erythema, increase tissue temperature, pain and impaired tissue function.

Important cellular components of the inflammatory response include polymorphonuclear leukocytes, mast cells, monocytes/macrophages and platelets. Polymorphonuclear leukocytes are the first inflammatory cells to appear at the site of injury, followed by monocytes and T lymphocytes. Enzymes are released from the polymorphonuclear leukocytes that may help remove necrotic tissue. Monocytes/macrophages are a direct source of vasoactive mediators, such as prostaglandins, leukotrienes and platelet activating factor. Also, monocytes release cytokines, such as, interleukin-1 (IL-1) and tumor necrosis factor-$\alpha$ (TNF-$\alpha$), to stimulate vascular invasion of the injured tissue and migration and proliferation of the mesenchymal cells that start the repair process.

Activation of these immune cells is receptor-specific. These receptors are cell-surface receptors which include G protein-linked seven-transmembrane domain receptors specific for either fMLP, lipid mediators, complement factors or chemokines, FC and complement receptors, CD14 and Toll-like receptors for lipopolysaccharide (LPS) and cytokine receptors for interferon-$\gamma$ (IFN-$\gamma$) and TNF-$\alpha$, Neutrophils and monocytes express additional activating receptors which bear some homology with activating natural killer (NK) cell receptors (Lanier, 1998). These receptor complexes are formed by the association of a type 1 glycoprotein DAP12 with receptors of the Ig superfamily (Bouchon et al., 2000; Dietrich et al., 2000) or the C-type lectin superfamily (Bakker et al., 1999; Lanier, et al., 1998). A noncovalent association is formed between a negatively charged amino acid residue located in the DAP12 transmembrane domain and a positively charged amino acid residue located in the transmembrane domain of these receptors. The signaling subunit of these complexes is located in the DAP12 intracellular domain since the intracellular domain of these receptors is too short to allow interaction with other molecules. Upon engagement of the receptor ligand-binding subunit, the DAP12 cytoplasmic Immunoreceptor Tyrosine-based Activation Motif (ITAM) initiates a cascade of phosphorylation events that leads to activation (Lanier et al., 1998; Campbell and Colonna, 1999). The monocytic receptors identified as DAP12-associating lectins are the Myeloid DAP12-associated Lectin (MDL-1), a novel receptor expressed exclusively in monocytes and macrophages (Bakker et al., 1999) and CD94/NKG2C, a receptor first identified in natural killer (NK) cells that binds to HLA-E (Lanier et al., 1998). The newly identified monocytic receptors of the Ig superfamily are the Triggering Receptor Expressed on Myeloid cells (TREM-1) and the Signal-Regulatory Protein $\beta$ 1 (SIRP $\beta$ 1) (Bouchon et al., 2000; Dietrich et al., 2000). TREM-1 is expressed on blood neutrophils and monocytes and is up-regulated by LPS. Triggering of TREM-1 induces neutrophil secretion of the inflammatory cytokine IL-8 and release of the myeloperoxidase (MPO), a granule component. In monocytes, the triggering of TREM-1 induces secretion of IL-8 and TNF-$\alpha$ cytokines, and the Monocyte Chemoattractant Protein (MCP-1) chemokine. In neutrophils and monocytes, triggering of TREM-1 also up-regulates the expression of several adhesion molecules involved in their extravasation.

Although inflammation can contribute to healing by facilitating removal of necrotic tissue and by initiating repair, it is not always beneficial. For example, an intense prolonged inflammatory response may increase the extent of tissue damage, delay repair, or cause excessive scarring, and it is not clear that successful healing requires inflammation. Thus, there is a general appreciation in the medical community that down regulation of the inflammatory response is needed in multiple medical situations in which the immune response causes tissue damage or provokes an unwanted reaction. In some specific medical situations, such as cancer treatment via monocyte-mediate immunotherapy, a strong activation of the immune response is desired. The present invention demonstrates for the first time a soluble form of the TREM-1 receptor. This soluble TREM-1 receptor could act as a down regulator by competing with the cell-surface TREM-1 receptor allowing the cell to limit the amount of activating signal it is receiving from the extracellular environment, thus modulating the inflammatory response.

SUMMARY OF THE INVENTON

A specific embodiment of the present invention is a method of modulating an immune response comprising the step of administering a compound to an animal to decrease and/or increase myeloid cell activation. Myeloid cell activation is decreased to modulate an inflammatory response and myeloid cell activation is increased to enhance tumor immunizations.

In specific embodiments, the immune response is an inflammatory response. The decrease in myeloid cell activation comprises decreasing the activity of DAP12/TREM-1 complex. Specifically, the compound is a competitive inhibitor of the ligand to TREM-1. It is contemplated that the competitive inhibitor is a polypeptide comprising the amino acid sequence of SEQ.ID.NO:2. Yet further, the inhibitor is a functional equivalent of the amino acid sequence of SEQ.ID.NO:2.

In a further embodiment, an inflammatory response is modulated by administering to an animal a compound that increases the levels of TREM-1sv in vivo.

Another specific embodiment is a method of decreasing myeloid cell activation comprising the step of administering to an animal a compound to decrease the activity of DAP12/TREM-1 complex. More particularly, the compound is a competitive inhibitor of the ligand for TREM-1. In specific embodiments, the competitive inhibitor is a polypeptide comprising an amino acid sequence of SEQ.ID.NO:2. It is also contemplated that the competitive inhibitor is a functional equivalent of the polypeptide comprising an amino acid sequence of SEQ.ID.NO:2. In further embodiments, the competitive inhibitor is admixed with a pharmaceutical carrier.

An addition embodiment of the present invention is a method of modulating an inflammatory response in a subject suffering from a disease or condition that results in inflammation comprising the step of altering the activity of the DAP12/TREM-1 complex. The activity of the DAP12/TREM-1 complex is altered by modulating the binding of a ligand to TREM-1. In specific embodiments, the binding of a ligand to TREM-1 is modulated by administering a competitive inhibitor for the ligand of TREM-1, wherein the competitive inhibitor is a polypeptide comprising SEQ.ID.NO:2 or a functional equivalent thereof. The competitive inhibitor can be administered via a parenteral route. Yet further, the binding of a ligand to TREM-1 is modulated by administering a compound that increases the levels of TREM-1sv, wherein TREM-1sv is a competitive inhibitor for the ligand of TREM-1.

In further embodiments, the disease or condition is selected from the group consisting of organ transplant/rejection, bone marrow transplant/rejection, graft versus host disease, infectious disease, autoimmune diseases. Specifically, the infectious disease is septic arthritis or septic shock.

Another embodiment of the present invention is a method of treating inflammation comprising the step of administering a compound comprising a pharmaceutical carrier admixed with a polypeptide of SEQ.ID.NO:2 or a functional equivalent thereof. The compound can be administered via a parenteral route, an alimentary route, topical, inhalation or intraarticular.

In specific embodiments of the present invention, it is provided a method of treating an autoimmune disorder comprising modulating the inflammatory response, wherein modulating comprises administering a compound comprising a polypeptide having the amino acid sequence of SEQ.ID.NO:2 or a functional equivalent thereof. Specifically, the autoimmune disorder is selected from the group consisting of rheumatoid arthritis, lupus and schleroderma. The polypeptide modulates the activity of DAP12/TREM-1 complex.

Another embodiment of the present invention is a method of modulating tissue healing/repair comprising the step of decreasing the inflammatory response, wherein decreasing comprises administering a compound comprising a polypeptide having the amino acid sequence of SEQ.ID.NO:2 or a functional equivalent thereof.

Another specific embodiment of the present invention is a method of modulating myeloid cell-mediated tumor immunotherapy comprising the step of administering a compound to an animal to decrease the levels of TREM-1 splice variant. Specifically, the compound comprises an antibody that binds immunologically to TREM-1 splice variant. Another compound includes, but is not limited to antisense RNA molecules of TREM-1 splice variant. The TREM-1 splice variant antibodies or antagonists can be used as adjuvants in cancer immunotherapy or vaccine trials to boost the immune response to tumor antigens.

In another embodiment of the present is a method of diagnosing an inflammatory response in a subject comprising the steps of: collecting a tissue sample from the subject; isolating monocytes from the sample; and measuring the levels of TREM-1 protein in the monocytes, wherein an increase in the levels of TREM-1 indicates an inflammatory response. Yet further, macrophages and/or neutrophils can be isolated from the tissue sample and the levels of TREM-1 protein in the macrophages and/or neutrophils is measured. The tissue sample can be bone marrow, however, any tissue sample may be used to measure macrophages.

In an addition embodiment, it is provided a method of diagnosing an inflammatory response in a subject comprising the steps of: collecting a blood sample from the subject; and measuring the levels if TREM-1 splice variant protein in the sample, wherein an decrease in the levels of TREM-1 splice variant indicates an inflammatory response.

In a further embodiment, the method comprises diagnosing an inflammatory response in a subject comprising the steps of: collecting blood and tissue samples from the subject; isolating monocytes and neutrophils from the tissue sample; measuring the levels of TREM-1 protein in the monocytes and neutrophils; and measuring the levels of TREM-1 splice variant in the blood sample, wherein an increase in the levels of TREM-1 protein and a decrease in the levels of TREM-1 splice variant indicates an inflammatory response.

Another specific embodiment of the present invention is a method of modulating the intensive cellular activation and phagocytic activity seen in disorders of the monocytic/macrophage cell lineage such as: Langerhans cell histiocytosis, and hemophagocytic lymphohistiocytosis (HLH). These (and other pathological entities) diseases represent both neoplastic and non-neoplastic disorders of the tissue histiocytes and/or monocytic lineage derived cells in which these cells through phagocytosis, inflammation, and release of toxic proteins destroy normal tissues and structures. These processes may be down regulated either by down regulating TREM-1 activation through up-regulation of the expression or presence of TREM-1 splice variant by any of the methods previously described. Alternatively TREM-1 activation may be down regulated by disruption of the DAP12/TREM-1 interaction or DAP12 signaling.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A shows RT-PCR products from CD34+ progenitor cells and mature CD14+ monocytes. FIG. 2B shows RT-PCR products from U937 cells (undifferentiated (U) and differentiated (D)), AML (FAB1 and FAB5) and ALL.

FIG. 4 illustrates TREM-1 and TREM-1 splice variant: nucleotide and predicted amino acid sequences. cDNA: The 193 base region that is spliced in the variant is in bold and underline. Protein: The hydrophobic signal peptide is in lower-case letter and the N+ indicates a potential N-glycosylation site. The small boxes contain the consensus sequences potentially involved in generating a disulfide bridge. The transmembrane domain is encased in the longer box.

DESCRIPTION OF THE EMBODIMENTS

Figure 1:
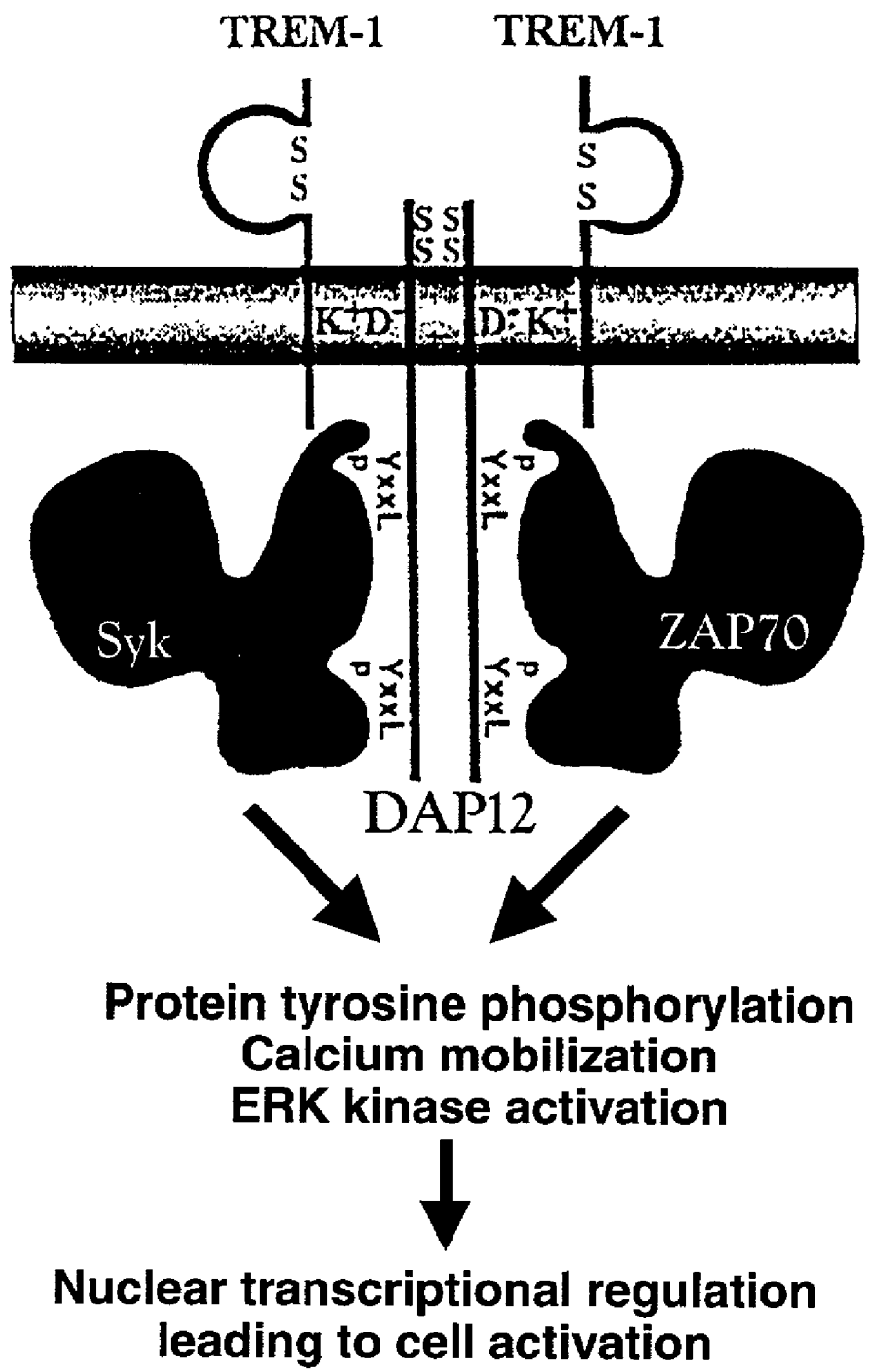
FIG. 1 is a schematic model of DAP12 and TREM-1. The disulfide-linked DAP12 homodimer displays two glutamic acid residues (D−) within the plasma membrane that have the potential capacity to interact with two lysine residues (K+) within the transmembrane-spanning domains of TREM-1. TREM-1 contains one extracellular imnmunoglobulin-like domain. Disulfide linkages are indicated (SS). Syk and ZAP70 kinases are depicted with their dual SH2 domains in association with the tyrosine phosphorylated ITAMs (pYxxL).

It is readily apparent to one skilled in the art that various embodiments and modifications may be made to the invention disclosed in this Application without departing from the scope and spirit of the invention.

As used herein the specification, "a" or "an" may mean one or more. As used herein in the claim(s), when used in conjunction with the word "comprising", the words "a" or "an" may mean one or more than one. As used herein "another" may mean at least a second or more.

The term "animal" or "subject", as used herein refers to mammals. More specifically, mammals include, but are not limited to, rats, mice, cats, dogs, monkeys and humans.

The term "antibody" as used herein, refers to an immunoglobulin molecule, which is able to specifically bind to a specific epitope on an antigen. As used herein, an antibody is intended to refer broadly to any immunologic binding agent such as IgG, IgM, IgA, IgD and IgE. Antibodies can be intact immunoglobulins derived from natural sources or from recombinant sources and can be immunoactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1988; Bird et al., 1988).

The term "autoimmune disease" or "autoimmune disorder" as used herein is defined as a disorder that results from an immune response directed at self antigens. Autoimmunity is an inappropriate and excessive response to self-antigens. Examples include, but are not limited to, Addison's disease, Graves' disease, multiple sclerosis, myxedema, pernicious anemia, rheumatic fever, rheumatoid arthritis, systemic lupus erythematosus, and ulcerative colitis.

The term "competitive inhibitor" as used herein is defined as a soluble form of the TREM-1 cell surface receptor that is capable of binding the ligand of TREM-1. Thus, one skilled in the art realizes that the "competitive inhibitor" includes variants of the TREM-1 receptor, for example, truncations, deletions, or substitutions which result in a soluble receptor. Yet further, the "competitive inhibitor" encompasses any splice variants of the TREM-1 receptor such as TREM-1sv.

The term "functional equivalent" as used herein is defined as a polynucleotide that has been engineered to contain distinct sequences while at the same time retaining the capacity to perform the biologic function of interest of the wild-type or reference protein. Thus, as used herein, the term functional equivalent includes truncations, deletions, insertions or substitutions of TREM-1 or TREM-1 splice variant which retains their function to antagonize the actions of the full-length, membrane bound TREM-1. This also can be accomplished to the degeneracy of the genetic code, i.e., the presence of multiple codons, which encode for the same amino acids. In one example, one of skill in the art may wish to introduce a restriction enzyme recognition sequence into a polynucleotide while not disturbing the ability of that polynucleotide to encode a protein. In another example, a polynucleotide may be (and encode) a functional equivalent with more significant changes. Certain amino acids may be substituted for other amino acids in a protein structure without appreciable loss of interactive binding capacity with structures such as, for example, antigen-binding regions of antibodies, binding sites on substrate molecules, receptors, and such like. So-called "conservative" changes do not disrupt the biological activity of the protein, as the structural change is not one that impinges of the protein's ability to carry out its designed function. It is thus contemplated by the inventors that various changes may be made in the sequence of genes and proteins disclosed herein, while still fulfilling the goals of the present invention.

The term "expression" as used herein is defined as the transcription and/or translation of a particular nucleotide sequence driven by its promoter.

The term "expression vector" as used herein refers to a vector containing a polynucleotide sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of control sequences, which refer to polynucleotide sequences necessary for the transcription and possibly translation of an operatively linked coding sequence in a particular host organism. In addition to control sequences that govern transcription and translation, vectors and expression vectors may contain polynucleotide sequences that serve other functions as well and are described infra.

The term "immune response" as used herein, is a general term that relates to the response made by the host to defend itself against a pathogen.

The term "inflammation" as used herein, is a general term for the local accumulation of fluid, plasma proteins, and white blood cells that is initiated by physical injury, infection or a local immune response. One skilled in the art is cognizant that inflammation is also known as an inflammatory response.

The term "leukocyte" as used herein is defined as a general term for a white blood cell. Leukocytes include lymphocytes, polymorphonuclear leukocytes, and monocytes.

The term "modulation" as used herein is defined as the capacity to either increase or decrease the immune response. The term is also used to refer to the pharmacological capacity to increase or decrease the immune response.

The term "monocyte" as used herein refers to white blood cells that circulate in the blood stream. Monocytes differentiate into macrophages upon migration into the tissues. Thus, as used in the present invention, the term "monocyte" also refers to macrophages.

The term "macrophage" as used herein refers to a large mononuclear phagocytic cell that is important in innate immunity, in early non-adaptive phases of host defense, as antigen presenting cells, and as effector cells in humoral and cell-mediated immunity. Macrophages are migratory cells deriving from bone marrow precursors and are found in most tissues in the body. Macrophage activation is important in controlling infection and also causes damage to neighboring tissues.

The term "myeloid cell" as used herein refers to monocytes, neutrophils and macrophages. Yet further, myeloid cell also refers to all stage differentiations of monocytes, macrophages and neutrophils.

The term "neutrophil" or "neutrophilic polymorphonuclear leukocyte" as used herein is the major class of white blood cells in peripheral blood. Neutrophils have an important role in engulfing and killing extracellular pathogens.

The term "natural killer cells" or "NK" as used herein is defined as large, usually granular non-T cell, non-B cell lymphocytes, which kill certain tumor cells. NK cells are important in innate immunity to viruses and other intracellular pathogens.

The term "pharmaceutically acceptable carrier" as used herein includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The term "polymorphonuclear leukocytes" as used herein is defined as white blood cells with multi-lobed nuclei and cytoplasmic granules. There are three types of polymorphonuclear leukocyte: neutrophils with granules that stain with neutral dyes, esoinophils with granules that stain with eosin, and basophils with granules that stain with basic dyes.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means. Furthermore, one skilled in the art is cognizant that polynucleotides include, without limitation, mutations of the polynucleotides, including but not limited to, mutation of the nucleotides, or nucleosides by methods well known in the art.

The term "polypeptide" as used herein is defined as a chain of amino acid residues, usually having a defined sequence. As used herein the term polypeptide is mutually inclusive of the terms "peptides" and "proteins". One of skill in the art is cognizant that polypeptides include, without limitation, mutations of polypeptides by methods that are well known in the art, i.e., site-directed mutagenesis or chemical mutagenesis.

The term "polynucleotide encoding a polypeptide" as used herein is defined to encompass polynucleotides that include a single continuous region or discontinuous regions encoding the polypeptide (for example, interrupted by introns) together with additional regions, that also may contain coding and/or non-coding sequences.

The term "promoter" as used herein is defined as a nucleic acid sequence recognized by the synthetic machinery of the cell, or introduced synthetic machinery, required to initiate the specific transcription of a polynucleotide sequence.

The term "transfected" or "transformed" or "transduced" as used herein refers to a process by which exogenous nucleic acid is transferred or introduced into the host cell. A transformed cell includes the primary subject cell and its progeny.

The phrase "under transcriptional control" or "operatively linked" as used herein means that the promoter is in the correct location and orientation in relation to the polynucleotides to control RNA polymerase initiation and expression of the polynucleotides.

The term "variant" or "variants" as used herein refers to polynucleotides or polypeptides that differ from a reference polynucleotide or polypeptide respectively. Variants in this sense are described below and elsewhere in the present disclosure in greater detail. For example, changes in the nucleotide sequence of the variant may be silent, i.e., they may not alter the amino acids encoded by the polynucleotide. Where alterations are limited to silent changes of this type a variant will encode a polypeptide with the same amino acid sequence as the reference polypeptide. Changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below. Generally, differences in amino acid sequences are limited so that the sequences of the reference and the variant are closely similar overall and, in many regions, identical. A variant and reference polypeptide may differ in amino acid sequence by one or more substitutions, additions, deletions, fusions and truncations, which may be present in any combination. A variant may also be a fragment of a polynucleotide or polypeptide of the invention that differs from a reference polynucleotide or polypeptide sequence by being shorter than the reference sequence, such as by a terminal or internal. deletion. For example, a variant may be a result of alternative mRNA splicing. Alternative mRNA splicing can lead to tissue-specific patterns of gene expression by generating multiple forms of mRNA that can be translated into different protein products with distinct functions and regulatory properties. These splice variants may occur by a mutation in an intron or exon or may be influenced post-transcriptionally. For example, the gene for inducible nitric-oxide synthase has the capacity to generate four mRNA isoforms by alternative mRNA splicing. These alternatively spliced mRNA transcripts are regulated in a tissue-specific manner and induced by cytokines (Eissa et al., 1996). Another variant of a polypeptide of the invention also includes a polypeptide which retains essentially the same function or activity as such polypeptide, e.g., proproteins which can be activated by cleavage of the proprotein portion to produce an active mature polypeptide. A variant may also be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. A variant of the polynucleotide or polypeptide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms, or may be made by recombinant means. Among polynucleotide variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions. All such variants defined above are deemed to be within the scope of those skilled in the art from the teachings herein and from the art.

The invention relates, inter alia, to polypeptides, polynucleotides, small molecules or variants thereof of a novel TREM-1 splice variant. The term TREM-1 splice variant and TREM-1sv are interchangeable. In specific embodiments, the invention relates to the TREM-1 splice variant having the nucleotide and amino acid sequences set out in SEQ.ID.NOS:1 and 2.

Polynucleotides

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

It is contemplated that nucleic acid sequences encoding the entire sequence of TREM or any fragment or variant thereof are within the scope of the present invention as set forth herein. The following nucleic acid sequences are sequences corresponding to TREM and are referenced with the corresponding GenBank Accession Numbers: *Mus musculus* TREM-2 (NM_021410; SEQ.ID.NO:3); *Mus musculus* TREM3 (NM_021407; SEQ.ID.NO:4); *Mus musculus* TREM1 (NM_021406; SEQ.ID.NO:5); homo sapiens TREM-2 (NM_018965; SEQ.ID.NO:6); homno sapiens TREM-1 (NM_018643; SEQ.ID.NO:7); homo sapiens TREM-1 (AF287008; SEQ.ID.NO:8); homo sapiens TREM-1 (AF196329; SEQ.ID.NO:9); *mus musculus* TREM-2(AF213458; SEQ.ID.NO:10); homo sapiens TREM-2 (AF213457; SEQ.ID.NO:11); *Mus musculus* TREM-3 (AF241220; SEQ.ID.NO:12); and *Mus musculus* TREM-1 (AF241219; SEQ.ID.NO:13).

Polynucleotides of the present invention which encode the polypeptide of SEQ.ID.NO:2 may include, but are not limited to, the coding sequence for the mature polypeptide, by itself, the coding sequence for the mature polypeptide and additional coding sequences, such as those encoding a leader or secretory sequence, such as a pre-, or pro- or prepro- protein sequence; and the coding sequence of the mature polypeptide, with or without the aforementioned additional coding sequences, together with additional, non-coding sequences, including, but not limited to, introns and non-coding 5' and 3' sequences, such as the transcribed, non-translated sequences that play a role in transcription, and mRNA processing, including splicing and polyadenylation signals, for example, for ribosome binding and stability of mRNA. Coding sequences which provide additional functionalities may also be incorporated into the polypeptide. Thus, for instance, the polypeptide may be fused to a marker sequence, such as a peptide, which facilitates purification of the fused polypeptide.

Further embodiments of the invention are polynucleotides that are at least 91% identical over their entire length to a polynucleotide encoding the TREM-1 splice variant polypeptide having the amino acid sequence set out in SEQ.ID.NO:2, and polynucleotides which are complementary to such polynucleotides. In this regard, polynucleotides at least 95% identical over their entire length to the same are particularly preferred, with those at least 97-99% being the most preferred.

The present invention also relates to vectors, which comprise a polynucleotide or polynucleotides of the present invention, and host cells, which are genetically engineered with vectors of the invention and the production of polypeptides of the invention by recombinant techniques. Host cells can be genetically engineered to incorporate polynucleotides and express polypeptides of the present invention. Introduction of polynucleotides into the host cell can be affected by calcium phosphate transfection, DEAE-dextran mediated transfection, transvection, microinjection, cationic lipid-mediated transfection, electroporation, transduction, scrape loading, ballistic introduction, infection or other methods. Such methods are described in many standard laboratory manuals, such as Davis, et al., 1986 and Sambrook, et al., 1989.

In the alternative to recombinant peptide synthesis, it is within the scope of the present invention to utilize other synthesizing techniques. Thus, the peptides of the invention can also be synthesized in solution or on a solid support in accordance with conventional techniques. Various automatic synthesizers are commercially available and can be used in accordance with known protocols. See, for example, Tam et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides.

One of skill in the art realizes that mature proteins can be expressed in mammalian cells, yeast, bacteria, or other cells under the control of appropriate promoters. These techniques use RNAs derived from the DNA constructs of the present invention. Appropriate cloning and expression vectors for use with prokaryotic and eukaryotic hosts are described by Sambrook, et al., 1989. Yet further, mature proteins can be expressed in a cell-free environment. Thus, it is within the scope of the present invention to employ cell-free translation systems or other biochemical synthesis processes to produce such proteins.

Another embodiment of the present invention comprises the use of polynucleotides for the purpose of expressing RNA transcripts that are not translated. For example, antisense RNA. Antisense methodology takes advantage of the fact that nucleic acids tend to pair with complementary sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA.

Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

As stated above, complementary or antisense means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

Also within the scope of the present invention is the use of polynucleotides to produce RNA enzymes or ribozymes. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et al., 1987; Forster and, Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Polypeptides

Another embodiment of the present invention relates to a soluble receptor splice variant of TREM-1. For example, the soluble receptor splice variant is the isolated polypeptide comprising the amino acid sequence of SEQ ID NO: 2.

The present invention demonstrates that the alternative splice variant of TREM-1 encodes a protein of 150 amino acids with a molecular mass of 17.5 kDa (FIG. 4). The first 136 amino acids of these 150 amino acids are identical to the TREM-1 first 136 amino acids but the last 14 amino acids are totally different. A hydrophobic signal peptide located at the beginning of the protein and two cysteines potentially generating an intrachain disulfide bridge characteristic of an Ig-superfamily V type fold, are conserved. Three potential N-linked glycosylation sites and the transmembrane region are missing. Thus, one of skill in the art is cognizant that without the transmembrane region, the cell-surface receptor is a soluble receptor.

The polypeptide of the present invention may be a recombinant polypeptide, a natural polypeptide or a synthetic polypeptide. Among certain embodiments of the invention, polypeptides comprise the amino acid sequence of TREM-1 splice variant, set out in SEQ.ID.NO:2, and variants thereof.

The present invention also includes, but is not limited to variants or biological functional equivalents of the TREM-1 splice variant. Among these variants are those of the TREM-1 splice variant polypeptide of SEQ.ID.NO:2 by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr.

Further variants may include fragments, having the amino acid sequence of the TREM-1 splice variant polypeptide of SEQ.ID.NO:2, in which several, 5 to 10, 1 to 5, 1 to 3, 2, 1 or no amino acid residues are substituted, deleted or added, in any combination. One of skill in the art is cognizant that such fragments or variants of TREM-1 splice variant will be biological functional equivalents, such as retaining similar ligand binding affinity or improved binding affinity.

In certain embodiments, it may be desirable to purify the polypeptides, subunit proteins or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

In addition to the biological functional equivalents discussed above, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al., (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

Other approaches have focused on the use of small, multi-disulfide-containing proteins as attractive structural templates for producing biologically active conformations that mimic the binding sites of large proteins (Vita et al., 1998). A structural motif that appears to be evolutionarily conserved in certain toxins is small (30-40 amino acids), stable, and high permissive for mutation. This motif is composed of a beta sheet and an alpha helix bridged in the interior core by three disulfides.

Beta II turns have been mimicked successfully using cyclic L-pentapeptides and those with D-amino acids. Weisshoff et al., (1999). Also, Johannesson et al., (1999) report on bicyclic tripeptides with reverse turn inducing properties.

Methods for generating specific structures have been disclosed in the art. For example, alpha-helix mimetics are disclosed in U.S. Pat. Nos. 5,446,128; 5,710,245; 5,840,833; and 5,859,184. Theses structures render the peptide or protein more thermally stable, also increase resistance to proteolytic degradation. Six, seven, eleven, twelve, thirteen and fourteen membered ring structures are disclosed.

Methods for generating conformationally restricted beta turns and beta bulges are described, for example, in U.S. Pat. Nos. 5,440,013; 5,618,914; and 5,670,155. Beta-turns permit changed side substituents without having changes in corresponding backbone conformation, and have appropriate termini for incorporation into peptides by standard synthesis procedures. Other types of mimetic turns include reverse and gamma turns. Reverse turn mimetics are disclosed in U.S. Pat. Nos. 5,475,085 and 5,929,237, and gamma turn mimetics are described in U.S. Pat. Nos. 5,672,681 and 5,674,976.

Antibodies

In certain aspects of the invention, one or more antibodies are produced to TREM-1 and TREM-1 splice variant. These antibodies may be used in various diagnostic or therapeutic applications. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

Assays

The present invention also relates to assays such as quantitative and qualitative assays for detecting levels of the TREM-1 splice variant protein, fragments or variants thereof in cells or in animals. Assay techniques that can be used to determine levels of a protein, such as a TREM-1 splice variant protein of the present invention, in a sample derived from a host are well-known to those of skill in the art. Such assay methods include radioimmunoassays, competitive-binding assays, Western Blot analysis and ELISA assays. An ELISA assay initially comprises preparing an antibody specific to the TREM-1 splice variant, preferably a monoclonal antibody. In addition, a reporter antibody generally is prepared which binds to the monoclonal antibody. The reporter antibody is attached a detectable reagent such as a radioactive, fluorescent or enzymatic reagent, in this example horseradish peroxidase enzyme.

Thus, a specific embodiment of the present invention comprises a method of diagnosing an inflammatory response in a subject comprising the steps of: collecting a tissue sample from the subject; isolating monocytes from the sample; and measuring the levels of TREM-1 protein in the monocytes, wherein an increase in the levels of TREM-1 indicates an inflammatory response. Yet further, macrophages and/or neutrophils can be isolated from the tissue sample and the levels of TREM-1 protein in the macrophages and/or neutrophils is measured. The tissue sample can be bone marrow, however, any tissue sample may be used to measure macrophages. Yet further, it is envisioned that the levels of TREM-1 splice variant protein in the sample can be measured and a decrease in the levels of TREM-1 splice variant indicates an inflammatory response.

To carry out an ELISA, a sample is removed from a host and incubated on a solid support, e.g., a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any TREM-1 splice variant proteins attached to the polystyrene dish. Unbound monoclonal antibody is washed out with buffer. The reporter antibody linked to horseradish peroxidase is placed in the dish resulting in binding of the reporter antibody to any monoclonal antibody bound to the TREM-1 splice variant. Unattached reporter antibody is then washed out. Reagents for peroxidase activity, including a calorimetric substrate, are then added to the dish. Immobilized peroxidase, linked to the TREM-1 splice variant through the primary and secondary antibodies, produces a colored reaction product. The amount of color developed in a given time period indicates the amount of the TREM-1 splice variant protein present in the sample. Quantitative results typically are obtained by reference to a standard curve.

A competition assay may be employed wherein antibodies specific to the TREM-1 splice variant attached to a solid support and labeled TREM-1 splice variant and a sample derived from the host are passed over the solid support. The amount of detected label attached to the solid support can be correlated to a quantity of TREM-1 splice variant in the sample.

This invention also provides a method for identification of binding molecules to the TREM-1 splice variant. Genes encoding proteins for binding molecules to the TREM-1 splice variant can be identified by numerous methods known to those of skill in the art, for example, ligand panning and FACS sorting. Such methods are described in many laboratory manuals such as, for instance, Coligan, et al., (1991) and Rivett, A. (1993).

In a specific embodiment, yeast two-hybrid analysis is performed by standard means in the art with the polypeptides of the present invention, i.e., TREM-1 splice variant. Two hybrid screen is used to elucidate or characterize the function of a protein by identifying other proteins with which it interacts. The protein of unknown function, herein referred to as the "bait" is produced as a chimeric protein additionally containing the DNA binding domain of GAL4. Plasmids containing nucleotide sequences which express this chimeric protein are transformed into yeast cells, which also contain a representative plasmid from a library containing the GAL4 activation domain fused to different nucleotide sequences encoding different potential target proteins. If the bait protein physically interacts with a target protein, the GAL4 activation domain and GAL4 DNA binding domain are tethered and are thereby able to act conjunctively to promote transcription of a reporter gene. If no interaction occurs between the bait protein and the potential target protein in a particular cell, the GAL4 components remain separate and unable to promote reporter gene transcription on their own. One skilled in the art is aware that different reporter genes can be utilized, including β-galactosidase, HIS3, ADE2, or URA3. Furthermore, multiple reporter sequences, each under the control of a different inducible promoter, can be utilized within the same cell to indicate interaction of the GAL4 components (and thus a specific bait and target protein). A skilled artisan is aware that use of multiple reporter sequences decreases the chances of obtaining false positive candidates. Also, alternative DNA-binding domain/activation domain components may be used, such as LexA. One skilled in the art is aware that any activation domain may be paired with any DNA binding domain so long as they are able to generate transactivation of a reporter gene. Furthermore, a skilled artisan is aware that either of the two components may be of prokaryotic origin, as long as the other component is present and they jointly allow transactivation of the reporter gene, as with the LexA system.

Two hybrid experimental reagents and design are well known to those skilled in the art (see The Yeast Two-Hybrid System by P. L. Bartel and S. Fields (eds.) (Oxford University Press, 1997), including the most updated improvements of the system (Fashena et al., 2000). A skilled artisan is aware of commercially available vectors, such as the Matchmaker™ Systems from Clontech (Palo Alto, Calif.) or the HybriZAP® 2.1 Two Hybrid System (Stratagene; La Jolla, Calif.), or vectors available through the research community (Yang et al., 1995; James et al., 1996). In alternative embodiments, organisms other than yeast are used for two hybrid analysis, such as mammals (Mammalian Two Hybrid Assay Kit from Stratagene (La Jolla, Calif.)) or E. coli (Hu et al., 2000).

In an alternative embodiment, a two hybrid system is utilized wherein protein-protein interactions are detected in a cytoplasmic-based assay. In this embodiment, proteins are expressed in the cytoplasm, which allows posttranslational modifications to occur and permits transcriptional activators and inhibitors to be used as bait in the screen. An example of such a system is the CytoTrap® Two-Hybrid System, from Stratagene (La Jolla, Calif.), in which a target protein becomes anchored to a cell membrane of a yeast which contains a temperature sensitive mutation in the cdc25 gene, the yeast homolog for hSos (a guanyl nucleotide exchange factor). Upon binding of a bait protein to the target, hSos is localized to the membrane, which allows activation of RAS by promoting GDP/GTP exchange. RAS then activates a signaling cascade which allows growth at 37° C. of a mutant yeast cdc25H. Vectors (such as pMyr and pSos) and other experimental details are available for this system to a skilled artisan through Stratagene (La Jolla, Calif.). (See also, for example, U.S. Pat. No. 5,776,689, herein incorporated by reference).

Thus, in accordance with an embodiment of the present invention, there is a method of screening for a peptide which interacts with TREM-1 and/or TREM-1 splice variant comprising introducing into a cell a first nucleic acid comprising a DNA segment encoding a test peptide, wherein the test peptide is fused to a DNA binding domain, and a second nucleic acid comprising a DNA segment encoding at least part of TREM-1, respectively, wherein the at least part of TREM-1, respectively, is fused to a DNA activation domain. Subsequently, there is an assay for interaction between the test peptide and the TREM-1 splice variant polypeptide or fragment thereof by assaying for interaction between the DNA binding domain and the DNA activation domain. For example, the assay for interaction between the DNA binding and activation domains may be activation of expression of β-galactosidase.

An alternative method is screening of .lambda.gt11, .lambda.LZAP (Stratagene) or equivalent cDNA expression libraries with recombinant TREM-1 splice variant. Recombinant TREM-1 splice variant protein or fragments thereof are fused to small peptide tags such as FLAG, HSV or GST. The peptide tags can possess convenient phosphorylation sites for a kinase such as heart muscle creatine kinase or they can be biotinylated. Recombinant TREM-1 splice variant can be phosphorylated with $^{32}[P]$ or used unlabeled and detected with streptavidin or antibodies against the tags. .lambda.gt11cDNA expression libraries are made from cells of interest and are incubated with the recombinant TREM-1 splice variant, washed and cDNA clones which interact with TREM-1 splice variant isolated. Such methods are routinely used by skilled artisans. See, e.g., Sambrook (supra).

Another method is the screening of a mammalian expression library in which the cDNAs are cloned into a vector between a mammalian promoter and polyadenylation site and transiently transfected in cells. Forty-eight hours later the binding protein is detected by incubation of fixed and washed cells with a labeled TREM-1 splice variant. In this manner, pools of cDNAs containing the cDNA encoding the binding protein of interest can be selected and the cDNA of interest can be isolated by further subdivision of each pool followed by cycles of transient transfection, binding and autoradiography. Alternatively, the cDNA of interest can be isolated by transfecting the entire cDNA library into mammalian cells and panning the cells on a dish containing the TREM-1 splice variant bound to the plate. Cells which attach after washing are lysed and the plasmid DNA isolated, amplified in bacteria, and the cycle of transfection and panning repeated until a single cDNA clone is obtained. See Seed et al., 1987 and Aruffo et al., 1987 which are herein incorporated by reference. If the binding protein is secreted, its cDNA can be obtained by a similar pooling strategy once a binding or neutralizing assay has been established for assaying supernatants from transiently transfected cells. General methods for screening supernatants are disclosed in Wong et al., (1985).

Another alternative method is isolation of proteins interacting with the TREM-1 splice variant directly from cells. Fusion proteins of TREM-1 splice variant with GST or small peptide tags are made and immobilized on beads. Biosynthetically labeled or unlabeled protein extracts from the cells of interest are prepared, incubated with the beads and washed with buffer. Proteins interacting with the TREM-1 splice variant are eluted specifically from the beads and analyzed by SDS-PAGE. Binding partner primary amino acid sequence data are obtained by microsequencing. Optionally, the cells can be treated with agents that induce a functional response such as tyrosine phosphorylation of cellular proteins. An example of such an agent would be a growth factor or cytokine such as interleukin-2.

Another alternative method is immunoaffinity purification. Recombinant TREM-1 splice variant is incubated with labeled or unlabeled cell extracts and immunoprecipitated with anti-TREM-1 splice variant antibodies. The immunoprecipitate is recovered with protein A-Sepharose and analyzed by SDS-PAGE. Unlabelled proteins are labeled by biotinylation and detected on SDS gels with streptavidin. Binding partner proteins are analyzed by microsequencing.

Further, standard biochemical purification steps known to those skilled in the art may be used prior to microsequencing.

Yet another alternative method is screening of peptide libraries for binding partners. Recombinant tagged or labeled TREM-1 splice variant is used to select peptides from a peptide or phosphopeptide library which interact with the TREM splice variant. Sequencing of the peptides leads to identification of consensus peptide sequences which might be found in interacting proteins.

Treatment

The present invention provides a method of modulating an immune response, such as but not limited to an inflammatory response, comprising the step of administering a compound to an animal to decrease myeloid cell activation. The animal or subject is preferably a mammal and more preferably a human.

It is envisioned that myeloid cell activation can be decreased by decreasing the activity of DAP12/TREM-1 complex by providing a compound that is a competitive inhibitor of the ligand to TREM-1. The competitive inhibitor can be a polypeptide comprising the amino acid sequence of SEQ.ID.NO:2 or a functional equivalent of the amino acid sequence of SEQ.ID.NO:2. The compound is administered to the animal in an amount effective to result in the modulation of the immune response.

In the present invention, myeloid cell activation comprises activation of monocytes, macrophages and/or neutrophils. The activation can be specific for monocytes/macrophages or specific for neutrophils. Yet further, myeloid cell activation may include a combination of activated monocytes, macrophages and neutrophils. Thus, it is envisioned that the present invention modulates the activation of monocytes, macrophages and/or neutrophils and any stage of differentiation of these cells.

The TREM-1 receptor contains a short intracellular domain that lacks docking motifs for signaling mediators. Thus, for TREM-1 to mediate activating signals, it must associate with an adapter molecule. The adapter molecule, such as DAP12, is a separate signal transduction subunit to mediate activating signals. TREM-1 comprises positively charged amino acids in its transmembrane domain, which allows for pairing with the negatively charged transmembrane domain of adapter molecules. The adapter molecules contain a cytoplasmic immunoreceptor tyrosine-based activation motif (ITAM), which upon phosphorylation, the adapter molecules recruit protein tyrosine kinases that lead to cell activation.

The present invention has identified the existence of a soluble circulating TREM-1 splice variant that can be used to help cells down regulate the DAP12/TREM-1 pathway and/or activation of the DAP12/TREM-1 complex. One of skill in the art realizes that the secretion of a receptor lacking the transmembrane domain is not able to transmit a signal to DAP12 and acts as a down regulator. It is envisioned that the TREM-1 splice variant down regulates the immune response by competing with the full length TREM-1 receptor for the ligand that binds to TREM-1. This competitive inhibition allows the cell to limit the amount of activating signal available to the fully functional receptor complex. Thus, the TREM-1 splice variant and similar molecules, such as functional equivalents, can be expected to modulate both the volume and potentially the kinetics of the resulting phosphorylation cascade.

It is known in the art that soluble forms of cell-surface receptors can down regulate or dampen the ligand mediated activation of cells by binding the ligand, thus making the ligand unavailable to the cell-surface receptor. An example similar to TREM-1 splice variant is sCD14. It is a soluble form of the CD14 cell-surface receptor (Tapping and Tobias, 2000). The soluble CD14 has been shown to inhibit the oxidative burst response of isolated human mononuclear cells, inhibit the LPS-induced TNF release and protect mice from LPS-induced lethality. Thus, a skilled artisan is cognizant that an increase in a soluble TREM-1 splice variant receptor or a functional equivalent can competitively compete for the ligand for cell-surface membrane TREM-1 receptor and decrease myeloid cell activation by down regulating the activity of the DAP12/TREM-1 complex.

In a further embodiment, it is envisioned that a compound that increases the levels of TREM-1sv can be administered to an animal to modulate the immune response. This compound increases the levels of TREM-1sv. Splice variants are well known and understood in the art, thus one of skill in the art is aware of various modifications that can be used to increase the levels of the splice variant. For example, the compound that is administered can act either pre or post-translationally to result in an increase in the TREM-1sv protein in vivo. The compound is a nucleic acid, a protein or a small molecule.

Another embodiment of the present invention is a method of decreasing myeloid cell activation comprising the step of administering to an animal a compound to decrease the activity of DAP 12/TREM-1 complex. The compound or competitive inhibitor is admixed with a pharmaceutical carrier. The compound is a competitive inhibitor of the ligand for TREM-1. The competitive inhibitor is a polypeptide comprising an amino acid sequence of SEQ.ID.NO:2 or a functional equivalent of the polypeptide comprising an amino acid sequence of SEQ.ID.NO:2.

This invention also provides a method of modulating an inflammatory response in a subject suffering from a disease or condition that results in inflammation comprising the step of altering the activity of the DAP12/TREM-1 complex by modulating the binding of a ligand to TREM-1. A competitive inhibitor for the ligand of TREM-1 is administered via a parenteral route to modulate the binding. The competitive inhibitor is a polypeptide comprising SEQ.ID.NO:2 or a functional equivalent thereof. Yet further, the competitive inhibitor is a soluble form of the cell-surface TREM-1 receptor. One of skill in the art is cognizant that the inhibitor can be a splice variant of TREM-1. Such splice variants can be produced by various modifications to the TREM-1 receptor. A natural splice variant has been isolated by the present invention. Also, included in the present invention are synthetic variants or synthetic functional equivalents of the natural splice variant. Deletion mutagenesis can be performed to confirm the specific region that is necessary to bind the ligand of TREM-1 and mediate the cellular response. Further, amino acid substitution may be utilized to alter transmembrane domain of TREM-1 to achieve a soluble form. Amino acid substitution may also be used to increase the binding affinity of the ligand to TREM-1 splice variant.

Yet further, this invention also provides a method of modulating an inflammatory response comprising the step of altering the activity of the DAP12/TREM-1 complex by modulating the binding of a ligand to TREM-1. A compound is administered to the animal to increase the levels of TREM-1sv. TREM-1sv is a competitive inhibitor for the ligand of TREM-1.

The disease or condition is selected from the group consisting of organ transplant/rejection, bone marrow transplant/rejection, graft versus host disease, infectious disease, autoimmune diseases. The infectious disease is septic arthritis or septic shock.

Another embodiment of the present invention is a method of treating inflammation comprising the step of administering a compound comprising a pharmaceutical carrier admixed with a polypeptide of SEQ.ID.NO:2 or a functional equivalent thereof. Administering is via a parenteral route, an alimentary route, topical, inhalation or intraarticular. One of skill in the art is aware that treating inflammation includes, but is not limited to modulating the immune response. The immune response may be modulated by decreasing myeloid cell activation. For example, a soluble form of a cell-surface receptor can be administered to an animal. One of skill in the art realizes that the soluble form of the receptor dampens the ligand mediated activation of cells by binding the ligand, thus making the ligand unavailable to the cell-surface receptor.

A specific embodiment is a method of treating an autoimmune disorder comprising modulating the inflammatory response, wherein modulating comprises administering a compound comprising a polypeptide having the amino acid sequence of SEQ.ID.NO:2 or a functional equivalent thereof. The autoimmune disorder is selected from the group consisting of rheumatoid arthritis, lupus and schleroderma. The polypeptide modulates the activity of DAP12/TREM-1 complex.

Another embodiment is a method of modulating tissue healing/repair comprising the step of decreasing the inflammatory response, wherein decreasing comprises administering a compound comprising a polypeptide having the amino acid sequence of SEQ.ID.NO:2 or a functional equivalent thereof. A skilled artisan is aware that a TREM-1 splice variant, the soluble receptor, may be useful to modulate tissue healing/damage after ischemic, thermal, or crush injuries because cytokines released by tissue macrophages, neutrophils, and other white cells serve to increase the ultimate scaring, dysfunction, and disfigurement of these biologic processes. Thus, if the release of the cytokines can be modulated, then scaring, dysfunction and disfigurement can be damped. Yet further, decreasing comprises administering a compound that increases the levels of TREM-1sv in vivo.

Another specific embodiment of the present invention is a method of modulating myeloid cell-mediated tumor immunotherapy comprising the step of administering a compound to an animal to decrease the levels of TREM-1 splice variant. For example, but not limited to, the compound comprises an antibody that binds immunologically to TREM-1 splice variant. It is contemplated that the antibody binds to a portion of TREM-1 splice variant and does not bind to TREM-1. Thus, the reduction of only TREM-1 splice variant can augment or increase the immune response. It is envisioned that TREM-1 splice variant antibodies or antagonists can be used as adjuvants in cancer immunotherapy or vaccine trails to boost the immune response to tumor antigens. It is also within the scope of the present invention that the reduction of TREM-1 splice variant can be beneficial to both inherited and acquired immunodeficiency states. Yet further, it is contemplated that the reduction of TREM-1 splice variant is equivalent to overexpression of TREM-1 or excess TREM-1, resulting in an increase in inflammation and an increase in the efficiency of the immunotherapy.

One of skill in the art is cognizant that other means of reducing TREM-1 splice variant is within the scope of the present application. For example, other compounds such as TREM-1 splice variant antisense RNA, ribozymes or other antagonists may be used. A skilled artisan realizes that both antisense RNA and RNA with ribozyme activity serve to reduce or eliminate expression of polynucleotides. Means for preparing antisense RNA and ribozymes are well known in the art and are discussed earlier in the present invention. Antisense RNA reduces production of the polypeptide product from the mRNA. Yet further, ribozymes may be produced which act as endoribonucleases and catalyze the cleavage of RNA molecules with selected sequences resulting in reduction of the polypeptide products. Thus, one of skilled in the art may use a variety of compounds to inhibit or reduce the expression of TREM-1 splice variant to increase the immune response.

Administration of compounds

Polypeptides and other compounds, for example, small molecules of the present invention may be employed alone or in conjunction with other compounds, such as therapeutic compounds.

The pharmaceutical forms suitable for injectable use include sterile aqueous solutions and/or dispersions; formulations including sesame oil, peanut oil and/or aqueous propylene glycol; and/or sterile powders for the extemporaneous preparation of sterile injectable solutions and/or dispersions. In all cases the form must be sterile and/or must be fluid to the extent that easy syringability exists. It must be stable under the conditions of manufacture and/or storage and/or must be preserved against the contaminating action of microorganisms, such as bacteria and/or fungi.

Solutions of the active compounds as free base and/or pharmacologically acceptable salts can be prepared in water suitably mixed with a surfactant, such as hydroxypropylcellulose. Dispersions can also be prepared in glycerol, liquid polyethylene glycols, and/or mixtures thereof and/or in oils. Under ordinary conditions of storage and/or use, these preparations contain a preservative to prevent the growth of microorganisms.

TREM-1 splice variant protein, polypeptide, peptide, small molecules, agonist and/or antagonist of the present invention can be formulated into a composition in a neutral and/or salt form. Pharmaceutically acceptable salts, include the acid addition salts (formed with the free amino groups of the protein) and/or which are formed with inorganic acids such as, for example, hydrochloric and/or phosphoric acids, and/or such organic acids as acetic, oxalic, tartaric, mandelic, and/or the like. Salts formed with the free carboxyl groups can also be derived from inorganic bases such as, for example, sodium, potassium, ammonium, calcium, and/or ferric hydroxides, and/or such organic bases as isopropylamine, trimethylamine, histidine, procaine and/or the like. In terms of using peptide therapeutics as active ingredients, the technology of U.S. Pat. Nos. 4,608,251; 4,601,903; 4,599,231; 4,599,230; 4,596,792; and/or 4,578,770, each incorporated herein by reference, may be used.

The carrier can also be a solvent and/or dispersion medium containing, for example, water, ethanol, polyol (for example, glycerol, propylene glycol, and/or liquid polyethylene glycol, and/or the like), suitable mixtures thereof, and/or vegetable oils. The proper fluidity can be maintained, for example, by the use of a coating, such as lecithin, by the maintenance of the required particle size in the case of dispersion and/or by the use of surfactants. The prevention of the action of microorganisms can be brought about by various antibacterial and/or antifungal agents, for example, parabens, chlorobutanol, phenol, sorbic acid, thimerosal, and/or the like. In many cases, it will be preferable to include isotonic agents, for example, sugars and/or sodium chloride. Prolonged absorption of the injectable compositions can be brought about by the use in the compositions of agents delaying absorption, for example, aluminum monostearate and/or gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the required other ingredients from those enumerated above. In the case of sterile powders for the preparation of sterile injectable solutions, the preferred methods of preparation are vacuum-drying and/or freeze-drying techniques which yield a powder of the active ingredient plus any additional desired ingredient from a previously sterile-filtered solution thereof. The preparation of more, and/or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and/or in such amount as is therapeutically effective. The formulations are easily administered in a variety of dosage forms, such as the type of injectable solutions described above, but drug release capsules and/or the like can also be employed.

For parenteral administration in an aqueous solution, for example, the solution should be suitably buffered if necessary and/or the liquid diluent first rendered isotonic with sufficient saline and/or glucose. These particular aqueous solutions are especially suitable for intravenous, intramuscular, subcutaneous and/or intraperitoneal administration. In this connection, sterile aqueous media which can be employed will be known to those of skill in the art in light of the present disclosure. For example, one dosage could be dissolved in 1 ml of isotonic NaCl solution and/or either added to 1000 ml of hypodermoclysis fluid and/or injected at the proposed site of infusion, (see for example, "Remington's Pharmaceutical Sciences" 15th Edition, pages 1035-1038 and/or 1570-1580). Some variation in dosage will necessarily occur depending on the condition of the subject being treated. The person responsible for administration will, in any event, determine the appropriate dose for the individual subject.

The active TREM-1 splice variant protein-derived peptides and/or agents may be formulated within a therapeutic mixture to comprise about 0.0001 to 1.0 milligrams, and/or about 0.001 to 0.1 milligrams, and/or about 0.1 to 1.0 and/or even about 10 milligrams per dose and/or so. Multiple doses can also be administered.

In addition to the compounds formulated for parenteral administration, such as intravenous, intraarticular and/or intramuscular injection, other pharmaceutically acceptable forms include, e.g., tablets and/or other solids for oral administration; liposomal formulations; time release capsules; and/or any other form currently used, including cremes.

One may also use nasal solutions and/or sprays, aerosols and/or inhalants in the present invention. Nasal solutions are usually aqueous solutions designed to be administered to the nasal passages in drops and/or sprays. Nasal solutions are prepared so that they are similar in many respects to nasal secretions, so that normal ciliary action is maintained. Thus, the aqueous nasal solutions usually are isotonic and/or slightly buffered to maintain a pH of 5.5 to 6.5. In addition, antimicrobial preservatives, similar to those used in ophthalmic preparations, and/or appropriate drug stabilizers, if required, may be included in the formulation. Various commercial nasal preparations are known and/or include, for example, antibiotics and/or antihistamines and/or are used for asthma prophylaxis.

Additional formulations which are suitable for other modes of administration include vaginal suppositories and/or pessaries. A rectal pessary and/or suppository may also be used. Suppositories are solid dosage forms of various weights and/or shapes, usually medicated, for insertion into the rectum, vagina and/or the urethra. After insertion, suppositories soften, melt and/or dissolve in the cavity fluids. In general, for suppositories, traditional binders and/or carriers may include, for example, polyalkylene glycols and/or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and/or the like. These compositions take the form of solutions, suspensions, tablets, pills, capsules, sustained release formulations and/or powders. In certain defined embodiments, oral pharmaceutical compositions will comprise an inert diluent and/or assimilable edible carrier, and/or they may be enclosed in hard and/or soft shell gelatin capsule, and/or they may be compressed into tablets, and/or they may be incorporated directly with the food of the diet. For oral therapeutic administration, the active compounds may be incorporated with excipients and/or used in the form of ingestible tablets, buccal tables, troches, capsules, elixirs, suspensions, syrups, wafers, and/or the like. Such compositions and/or preparations should contain at least 0.1% of active compound. The percentage of the compositions and/or preparations may, of course, be varied and/or may conveniently be between about 2 to about 75% of the weight of the unit, and/or preferably between 25-60%. The amount of active compounds in such therapeutically useful compositions is such that a suitable dosage will be obtained.

The tablets, troches, pills, capsules and/or the like may also contain the following: a binder, as gum tragacanth, acacia, cornstarch, and/or gelatin; excipients, such as dicalcium phosphate; a disintegrating agent, such as corn starch, potato starch, alginic acid and/or the like; a lubricant, such as magnesium stearate; and/or a sweetening agent, such as sucrose, lactose and/or saccharin may be added and/or a flavoring agent, such as peppermint, oil of wintergreen, and/or cherry flavoring. When the dosage unit form is a capsule, it may contain, in addition to materials of the above type, a liquid carrier. Various other materials may be present as coatings and/or to otherwise modify the physical form of the dosage unit. For instance, tablets, pills, and/or capsules may be coated with shellac, sugar and/or both. A syrup of elixir may contain the active compounds sucrose as a sweetening agent methyl and/or propylparabens. as preservatives, a dye and/or flavoring, such as cherry and/or orange flavor.

In certain embodiments, the use of lipid formulations and/or nanocapsules is contemplated for the introduction of a TREM-1 splice variant protein, polypeptides, peptides and/or agents, and/or gene therapy vectors, including both wild-type and/or antisense vectors, into host cells.

Nanocapsules can generally entrap compounds in a stable and/or reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention, and/or such particles may be easily made.

In an embodiment of the invention, the polypeptides or fragments of TREM-1 or TREM-1 splice variant may be associated with a lipid. The polypeptides associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid or lipid/polypeptide associated compositions of the present invention are not limited to any particular structure in solution. For example, they may be present in a bilayer structure, as micelles, or with a collapsed structure. They may also simply be interspersed in a solution, possibly forming aggregates which are not uniform in either size or shape Lipids are fatty substances which may be naturally occurring or synthetic lipids. For example, lipids include the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes.

Phospholipids may be used for preparing the liposomes according to the present invention and may carry a net positive, negative, or neutral charge. Diacetyl phosphate can be employed to confer a negative charge on the liposomes, and stearylamine can be used to confer a positive charge on the liposomes. The liposomes can be made of one or more phospholipids.

A neutrally charged lipid can comprise a lipid with no charge, a substantially uncharged lipid, or a lipid mixture with equal number of positive and negative charges. Suitable phospholipids include phosphatidyl cholines and others that are well known to those of skill in the art.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

Phospholipids can form a variety of structures other than liposomes when dispersed in water, depending on the molar ratio of lipid to water. At low ratios the liposome is the preferred structure. The physical characteristics of liposomes depend on pH, ionic strength and/or the presence of divalent cations. Liposomes can show low permeability to ionic and/or polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and/or results in an increase in permeability to ions, sugars and/or drugs.

Liposomes interact with cells via four different mechanisms: Endocytosis by phagocytic cells of the reticuloendothelial system such as macrophages and/or neutrophils; adsorption to the cell surface, either by nonspecific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

Liposome-mediated oligonucleotide delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the lipid may be associated with a hemagglutinating virus (HVJ). This has been shown to facilitate fusion with the cell membrane and promote cell entry of liposome-encapsulated DNA (Kaneda et al., 1989). In other embodiments, the lipid may be complexed or employed in conjunction with nuclear non-histone chromosomal proteins (HMG-1) (Kato et al., 1991). In yet further embodiments, the lipid may be complexed or employed in conjunction with both HVJ and HMG-1. In that such expression vectors have been successfully employed in transfer and expression of an oligonucleotide in vitro and in vivo, then they are applicable for the present invention. Where a bacterial promoter is employed in the DNA construct, it also will be desirable to include within the liposome an appropriate bacterial polymerase.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Liposomes within the scope of the present invention can be prepared in accordance with known laboratory techniques. In one preferred embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

In the alternative, liposomes can be prepared in accordance with other known laboratory procedures: the method of Bangham et al., (1965), the contents of which are incorporated herein by reference; the method of Gregoriadis, as described in DRUG CARRIERS IN BIOLOGY AND MEDICINE, G. Gregoriadis ed. (1979) pp. 287-341, the contents of which are incorporated herein by reference; and the reverse-phase evaporation method as described by Szoka and Papahadjopoulos (1978). The aforementioned methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated nucleic acid is removed by centrifugation at 29,000×g and the liposomal pellets washed. The washed liposomes are resuspended at an appropriate total phospholipid concentration, e.g., about 50-200 mM. The amount of nucleic acid encapsulated can be determined in accordance with standard methods. After determination of the amount of nucleic acid encapsulated in the liposome preparation, the liposomes may be diluted to appropriate concentrations and stored at 4° C. until use.

A pharmaceutical composition comprising the liposomes will usually include a sterile, pharmaceutically acceptable carrier or diluent, such as water or saline solution.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

U937 Cell Differentiation

U937 cells (American Type Culture Collection, Rockville, Md.) were differentiated with 1α, 25-dihydroxyvitamin D3 (D3) (Sigma, St. Louis, Mo.) and recombinant human TGF-β1 (R&D Systems, Minneapolis, Minn.) added at a daily concentration of 250 ng/ml (60 nM) and 1 ng/ml, respectively during 4 days. (Gingras and Margolin, 2000).

Example 2

Cell Isolation

Human bone marrow CD34+ stem cell and peripheral blood-derived CD14+ mature monocyte are isolated as described by Gingras and Margolin (2000). The purity of the CD34+ and CD14+ cell preparation was confirmed by FACS analysis to be greater than 90% and 98%, respectively. Leukopheresis samples of patients diagnosed with pre-B Acute Lymphoblastic Leukemia (ALL) and Acute Myelogenous Leukemia (AML) FAB1 and FAB5 were fractionated on a polysucrose gradient (Histopaque, Sigma) and cells were collected at the interface.

Example 3

Construction and Screening of the Subtracted Library

A subtracted library was constructed and screened as described by Gingras and Margolin (2000). In brief, total cellular RNA and mRNA were extracted with Ultraspec II (Biotecx Laboratories, Houston, Tex.) and Oligotex (Qiagen, Santa Clarita, Calif.), respectively. The PCR-based cDNA subtraction method was performed on the undifferentiated versus differentiated U937 cells (Diatchenko et al., 1996 and Gurskaya et al., 1996). Amplified, subtracted treated cell cDNAs were ligated to pT7Blue vector and transformed into NovaBlue competent cells (Novagen, Madison, Wis.). Screening for differentially expressed genes was performed using the PCR-Select differential screening kit (Clontech Laboratories, Palo Alto, Calif.). TREM-1 and MDL-1 were obtained as a 713 and 498 base Rsa I fragment, respectively.

Example 4

Dot Blot Analysis

Clontech's multiple tissue expression array (MTE) was hybridized overnight at 65° C. with Strip-EZ $^{32}$P-labeled probes (Ambion, Austin, Tex.) using ExpressHyb (Clontech) hybridization solution. The array was washed as recommended (65° C., 5×20 min in 2×SSC/1% SDS and 55° C., 2×20 min in 0.1×SSC/0.5% SDS), and exposed to Kodak X-OMAT AR film.

TREM-1 and MDL-1 expression distribution was analyzed with Clontech's multiple tissue expression array. TREM-1 expression was more elevated in the peripheral blood leukocyte than in the bone marrow but MDL-1 expression was slightly higher in the bone marrow than in the peripheral blood leukocytes. TREM-1 and MDL-1 expression was also detected in the lymph node. TREM-1 was more highly expressed in adult liver, lung, and spleen than in the corresponding fetal tissue, MDL-1 was more highly expressed in adult than fetal liver and lung tissue. TREM-1 was also expressed in placenta, spinal cord and heart tissues.

Example 5

TREM-1, MDL-1 and DAP12 Gene Expression in CD34+ and CD14+ Cells, U937 Cells, AML and ALL Patients TREM-1, MDL-1, and DAP12 gene expression was analyzed in several cell types. One µg CD34+ and CD14+ total RNA, and one hundred ng U937, AML and ALL mRNA were reverse transcribed in the presence of oligo dT in a volume of 20 µl. One µl of cDNA was amplified in a volume of 25 µl with GAPDH primer set for 20 cycles, with TREM-1 primer sets for 25 cycles (CD34+ and CD14+ cells) or for 32 cycles (U937, AML, and ALL cells), with MDL-1 primer set for 30 cycles, and with DAP12 primer set for 26 cycles. The following primer sets were used.

TREM-1 primer sets: designed to detect the expression of the normal as well as the splice variant; the location relates to TREM-1 sequence mentioned in FIG. 4.—(SEQ.ID.NO:14; sense primer) 5' GGACGGAGAGATGCCCAAGACC 3' (bases 241 to 262) and (SEQ.ID.NO:15; antisense primer) 5' ACCAGCCAGGAGAATGACAATG 3' (bases 679 to 700) (CD34+ and CD14+ cells)—(SEQ.ID.NO:16; sense primer) 5' CAGAGAGGCCTTCAAAGAAT 3' (bases 273 to 292) with the (SEQ.ID.NO:17; antisense primer) 5' CCTCCCT-TGGCACAACT 3' (bases 821 to 837) (U937, AML, and ALL cells). MDL-1 primer set:—(SEQ.ID.NO:18; sense primer) 5' TGTGGAGGATTTGAAGTTGAG 3' and (SEQ.ID.NO: 19: antisense primer) 5' CGTGAGTCTAAGGGTTG-GATGG 3' DAP12 primer set:—(SEQ.ID.NO:20; sense primer) 5' ATCCCACCGGCCCTTACACT 3' and (SE-Q.ID.NO:21; antisense primer) 5' GGGGAGCGGTCTG-GTCTCT 3' GAPDH primer set: purchased from Clontech.

RT-PCR was done in parallel on progenitor CD34+ stem cells and mature CD14+ monocytes and showed a marked increase of TREM-1, MDL-1, and DAP12 expression in mature monocytes (FIG. 2A). For each gene, the number of PCR cycles necessary to detect any expression in the progenitor cells was greater than the number of cycles needed to reach the PCR plateau in mature CD14+ monocytes. In undifferentiated U937 cells, TREM-1, MDL-1 and DAP12 expression was not or barely detected by Northern but was apparent by RT-PCR (FIG. 2B and FIG. 3) By contrast, based on the signal obtained on the Northern blots, TREM-1, MDL-1, and DAP12 were highly expressed in differentiated U937 cells (FIG. 3).

Figure 2:
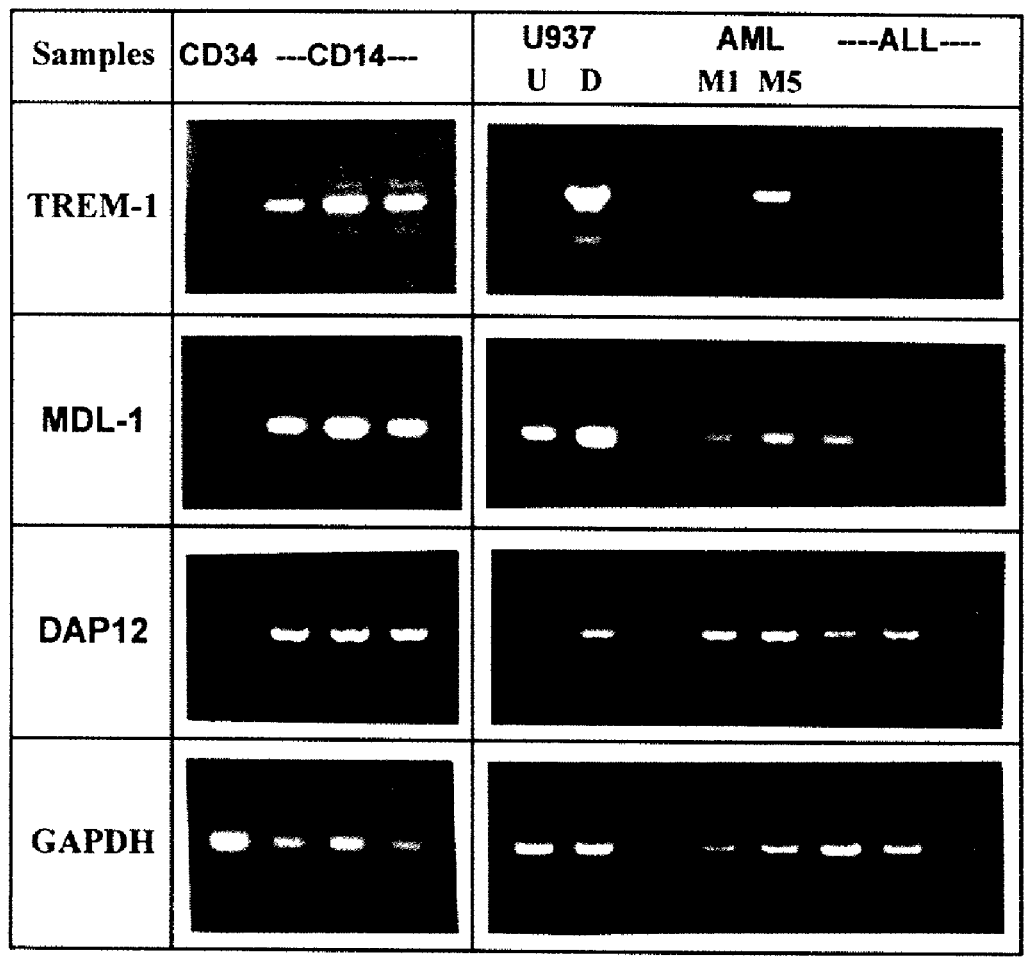
FIG. 2A and FIG. 2B illustrate RT-PCR product of TREM-1, TREM-1 splice variant, MDL-1, and DAP12 expression.
Figure 3:
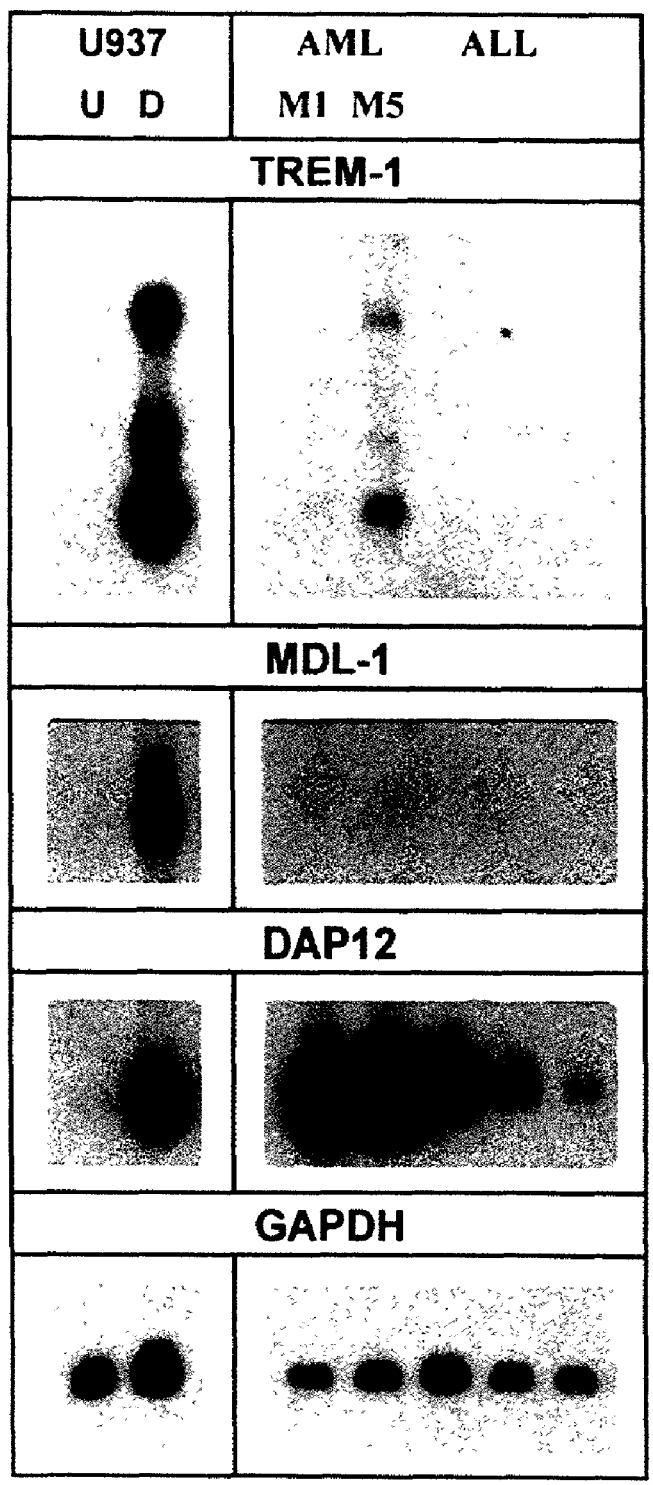
FIG. 3 illustrates a Northern analysis of TREM-1, MDL-1 and DAP12 expression in U937 cells (undifferentiated (U) and differentiated (D)), AML (FAB1 and FAB5), and ALL.

TREM-1 and DAP12 expression in AML FAB1 and FAB5 cells was detectable by Northern and was stronger in the differentiated FAB5 than in FAB1 cells (FIG. 3). MDL-1 expression in AML cells was barely detectable by Northern but was detected by RT-PCR (FIG. 2B and FIG. 3). However, MDL-1 and DAP12 expression was only slightly higher in FAB5 cells. Expression of TREM-1, MDL-1, and DAP12 was also detected in ALL by RT-PCR (FIG. 2B).

Example 6 cDNA Full-Length Detection

The TREM-1 cloned fragment was amplified by PCR using 5' end biotinylated nested primer 1 and nested primer 2R. These primers were located in the adaptors linked to all the cDNA used for suppression subtractive hybridization (SSH) (Gingras and Margolin, 2000). The resulting biotinylated probe was run on a 2% agarose gel and purified using the Ultrafree-MC centrifugal filter units (Millipore, Bedfort, Mass.). One hundred ng of biotinylated probe and one µg of amplified, differentiated U937 cDNA (SMART cDNA, Clontech) were denatured together, mixed with the Dynabeads kilobaseBINDER binding solution (Dynal, Lake Success, N.Y.) and hybridized overnight at 65° C. The biotinylated hybrids were then incubated 3 hours with 50 µg of Dynabeads M280 Streptavidin. Two 15-minute washes were done with 0.1×SSC, 0.1% SDS at room temperature, and three 15-minute washes were done at 65° C. The full-length cDNAs were eluted for 5 min at 95° C. in water and amplified with the PCR primer from the SMART PCR cDNA synthesis kit (Clontech). The hybridization was repeated 2 more times with 100 ng of biotinylated probe and 100 ng of amplified selected cDNA. The full-length cDNA were cloned in pCR2.1 vector (TA cloning kit, Invitrogen, San Diego, Calif.), identified by PCR and sequenced.

To confirm that the sequence obtained from U937 cells does not contain any mutations, one µg of CD14+ total RNA was reverse transcribed with oligo dT and the cDNA amplified with the following sets of primers. Primer location relates to FIG. 4.—5' end set: (SEQ.ID.NO:22; sense primer) 5' GGAGCCCTCAGCAGCAGTTG 3' (bases 26 to 45) and (SEQ.ID.NO:23; antisense primer) 5' TTGGGTGGAGCT-TGGGTCAC 3' (bases 578 to 597)—3' end set: (SEQ.ID.NO: 16; sense primer) 5' CAGAGAGGCCTTCAAAGAAT 3' (bases 273 to 292) and (SEQ.ID.NO:24; antisense primer) 5' TTTAAGGTGAGACGCTGACT 3' (bases 904 to 923).

TREM-1 and TREM-1 splice variant were isolated for sequencing by cloning PCR products in pCR2.1 vector (TA cloning kit, Invitrogen).

Example 7

Intron Analysis: Confirmation of Alternative Splicing in TREM-1 Splice Variant

Blood from a normal individual was fractionated on a polysucrose gradient (Histopaque, Sigma) and mononuclear cells (PBMC) collected at the interface. PBMC genomic DNA was extracted with QIAamp DNA mini kit (Qiagen). A RT-PCR on the differentiated U937 cell mRNA and a PCR on the normal PBMC genomic DNA were done in parallel with the following primer sets designed to flank the assumed 5' and 3' junction sites.—5' junction set: (SEQ.ID.NO:25; sense primer) 5' CGAATGGTCAACCTTCAAG 3' (bases 359 to 377) and (SEQ.ID.NO:26; antisense primer) 5' CTGGTATA-GAGTGGGCACAA 3' (bases 548 to 567)—3' junction set: (SEQ.ID.NO:27; sense primer) 5' AAGCTCCACCCAAGT-CAACTGC 3' (bases 585 to 606) and (SEQ.ID.NO:15 antisense primer) 5' ACCAGCCAGGAGAATGACAATG 3' (bases 679 to 700).

Automated sequencing reactions were performed.

Example 8

Three Sizes of TREM-1 mRNA

Northern blots were prepared with 1.65 µg of mRNA electrophoresed on a 1% formaldehyde gel and downward transferred on a nylon membrane (BrightStar-Plus, Ambion, Austin, Tex.) (Gingras and Margolin, 2000) and hybridized overnight at 65° C. with Strip-EZ $^{32}$P-labeled probes (Ambion, Austin, Tex.) using ExpressHyb (Clontech) hybridization solution. The membrane was washed as recommended (65° C., 5×20 min in 2×SSC/1% SDS and 55° C., 2×20 min in 0.1×SSC/0.5% SDS), and exposed to film.

Northern blots hybridized with TREM-1, DAP12 and MDL-1 Rsa I fragments resulted in the detection of three different size of TREM-1 mRNAs (~950, ~1,700 and ~3,500 bases), and of a ~3,500 base MDL-1 mRNA, and of a ~750 base DAP12 mRNA in the differentiated U937 cells (FIG. 3).

Example 9

TREM-1 and TREM-1 Splice Variant

The TREM-1 cloned sequence was isolated from the SSH library as a 713 base Rsa I fragment. TREM-1 (SEQ.ID.NO: 8) full-length sequence of 948 bases was obtained by indirect hybrid capture on differentiated U937 cells and was confirmed in the normal CD14+cells (FIG. 4). The 948 base sequence was identical to 854 bases of the 884 bases recently published by Bouchon, Dietrich, and Colonna (SEQ.ID.NO:

9). It differed in the length of the 5' non-coding region (64 bases compared to 47 bases before the ORF) and of the 3' non-coding region which reached the polyadenylation site. The 30 base discrepancy between the two sequences was in the 5' non-coding region: the first 30 bases published by Bouchon et al sequence shared no homology with the first 47 base sequence obtained in U937 and CD14+cells. In CD14+ cells, amplification with a 5' end primer set resulted in a product perfectly matching the TREM-1 sequence obtained in U937 cells. This primer set consisted of a sense primer located in the 5' non-coding region (bases 26 to 45) paired with an antisense primer located 578 bases inside the sequence (FIG. 4). The sense primer had no homology with Bouchon et al TREM-1 first 30 base sequence. This result validates the 5' non-coding region sequence described in FIG. 4. Furthermore, SEQ.ID.NO:8; TREM-1 sequence (including the 5' non-coding region) correlated with information available in the unfinished Human Genome sequences (htgs) of GenBank (accession number AC023320).

Primer sets consisting of a sense primer located within the first 300 bases paired with an antisense primer located at or after 679 bases amplified not only the expected size of TREM-1 sequence, but also an unexpected shorter product (FIG. 2). That variant was detected by RT-PCR in progenitor CD34+ cells (elevated PCR cycles), mature CD14+ monocytes, differentiated U937 cells, and AML cells. It was not detected by RT-PCR in undifferentiated U937 or ALL cells under the experimental condition used. It was not detected as an individual band in Northern due to the proximity of migration between mRNAs separated by less than 200 bases, and the intensity of the 950 base band.

Figure 5:
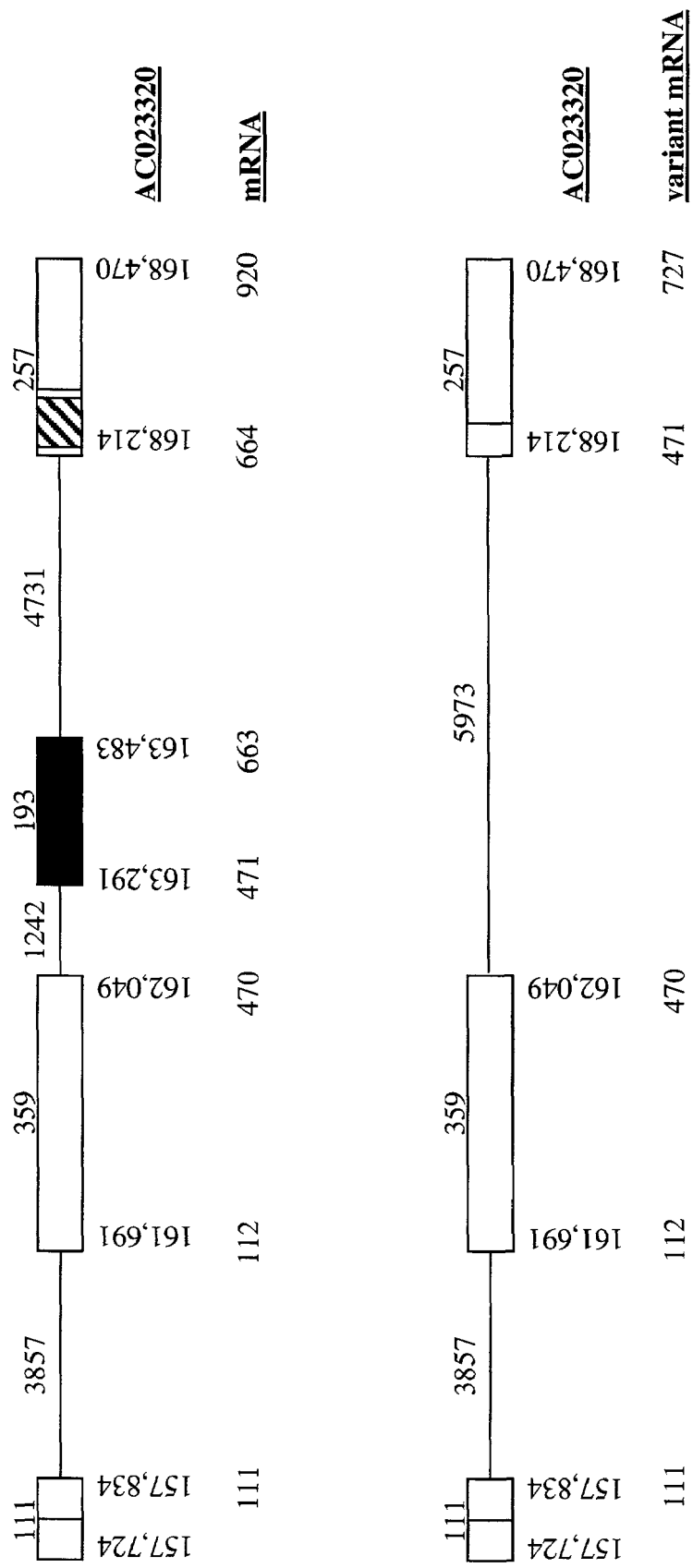
FIG. 5 illustrates a graphical representation of TREM-1 genomic structure and mRNA processing. Boxes represent the location of the 4 exons as determined by TREM-1 cDNA sequence in correlation with GenBank genomic sequence accession number AC023320. Gray and hatched area represents untranslated regions and the transmembrane domain, respectively. The variant spliced exon is filled in black. Horizontal numbers indicate the exon and intron size. Vertical numbers correspond to the exon and intron location in the genomic sequence (AC023320).

After sequencing, this product was identified as a TREM-1 splice variant (SEQ.ID.NO:1) containing a 193 base deletion from bases 471 to 663 (FIG. 4). The bases at both borders of the deleted sequences (CAAGG and CAGG) match the consensus sequence of a cDNA splice junction (Mount, 1982). The CAAG and CAG sequences originate from the 3' end of an exon splicing junction link to the first G of the 5' end adjacent exon. This indicates that the variant was obtained by the alternative splicing of an exon. Next, primer sets were designed to cover each splicing border. PCR on normal genomic DNA resulted in the amplification of approximately 1,400 and 4,800 base pair products. This corresponds with the result obtained from BLAST analysis using TREM-1 cDNA against the unfinished Human Genome sequences (htgs) of GenBank (Altschul et al., 1997). This search identified the location of 4 exons and 3 introns in TREM-1 genome (Genbank accession number AC023320) and confirmed once more that the sequence deleted in the variant was an exon that was in fact the third TREM-1 exon (FIG. 5).

Example 10

Diagnostic Uses of TREM-1 Splice Variant

The levels of TREM-1 splice variant are measured in samples collected from normal individuals and individuals suffering from an autoimmune disease. The samples that are collected are samples of whole blood and bone marrow. Monocytes and neutrophils are isolated using standard procedures well known in the art and the levels of TREM-1 protein are measured in the monocytes and neutrophils. The levels of TREM-1 splice variant, which is the circulating and soluble form of TREM-1, is measured in the blood samples.

Samples are analyzed for abnormal quantities of TREM-1 on monocytes and neutrophils and abnormal amounts of TREM-1sv excreted in the blood.

Yet further, one of skill in the art realizes that macrophages can be isolated from tissue samples and TREM-1 and/or TREM-1 splice variant is measured in the isolated macrophages. Tissue samples that may be used include all tissues.

Example 11

In vitro Functional Assay

In vitro activation of the immune response is blocked by flooding the system with TREM-1 splice variant protein.

Immunologic cell lines are used for the in vitro studies. The cells are plated and grown to confluency. Once the cells are confluent, then a stimulator or inducer is added to induce an immune response, such as cytokine production. Stimulators, such as LPS, are well known and used in the art. LPS is added to the confluent cells. Upon stimulation, cytokine production is measured. Next, TREM-1 splice variant is added to the cells. After a period of incubation, cytokine production is measured. A decrease in cytokine production indicates that TREM-1 splice variant down-regulated the immune response.

Variations to this in vitro method are within the scope of the present invention. For example, LPS and TREM-1 splice variant are added to confluent cells simultaneously. After an incubation period, cytokine levels are measured. Cytokine levels similar to unstimulated, untreated cells indicate that the simultaneous addition of TREM-1 splice variant inhibited the initiation of the immune response.

Example 12

In vivo Blockage of Inflammatory Response

The inflammatory response is blocked in vivo by flooding the system with TREM-1 splice variant protein.

TREM-1 splice variant polypeptide is administered intravenously to an animal suffering from an inflammatory response. The polypeptide is administered as a peptide pharmaceutical or in combination with a pharmaceutical carrier.

TREM-1 splice variant polypeptide is administered directly to the site of inflammation.

It is envisioned that the administration of excess TREM-1 splice variant may result in down regulation of the inflammatory response.

Example 13

Modulation of Inflammation in Septic Shock

It is envisioned that TREM-1 splice variant or a variant is a potential therapy for septic shock.

Mice are injected intraperitoneally with different concentrations of LPS. TREM-1 splice variant polypeptide or other competitive inhibitor of the ligand for TREM-1 is administered to the animal at 1, 2, 4 and 6 hours after the LPS administration.

Another alternative is to administer to the animal TREM-1 splice variant polypeptide or other competitive inhibitor of the ligand for TREM-1 hr prior to LPS administration.

In both examples, it is envisioned that the administration of the TREM-1 splice variant results in a down regulation of the inflammatory response preventing shock and death. Thus, administration of a soluble TREM-1 is a suitable therapy for the treatment of septic shock as well as other inflammatory diseases.

Example 14

Structure Function Studies

Structure function studies are performed by expressing mutants of TREM-1 splice variant using standard transient transfection techniques that are well known and used in the art. Regions of TREM-1 splice variant are deleted and the ability of the mutant to inhibit activation of cells in the presence of a stimulator is measured. Specific measurements include, but are not limited to pro-inflammatory chemokines and cytokines, calcium mobilization and tyrosine phosphorylation.

In addition to performing structure studies using mutants of TREM-1 splice variant, similar structure studies are performed by expressing mutants of TREM-1.

Example 15

Modulation of Monocyte-Mediated Killing of Tumor Cells by TREM-1 Splice Variant Leukemic cells (target cell) such as K562, U937, and KG-1 are pooled with monocytes (effector cell) at an effector target ratio of 12:1 at $10^5$ cells/ml. The plates are centrifuged at 200×g to encourage cell conjugation and incubated at 37° C. for 24 hours with the one of the following groups of reagents: control; TREM-1 splice variant; anti-TREM-1 antibody (or TREM-1 ligand); anti-TREM-1 antibody and TREM-1 splice variant; GM-CSF; GM-CSF and TREM-1 splice variant; LPS; LPS and TREM-1 splice variant; GM-CSF and LPS; GM-CSF, LPS, and TREM-1 splice variant.

Monocyte-mediated killing is measured by an MTT cytotoxicity assay.

It is contemplated that TREM-1 splice variant can inhibit leukemic cell killing by monocytes that are activated though different pathways, i.e., DAP12/TREM-1 or TNF.

Example 16

Modulation of Monocyte-Mediated Tumor Immunotherapy

It is envisioned that down modulation of TREM-1 splice variant during the course of monocyte-mediated tumor immunotherapy may increase the efficiency of the treatment.

Antibodies are developed to the tail portion of TREM-1 splice variant. These antibodies bind TREM-1 splice variant, but do not bind TREM-1. The antibodies are administered to an animal with tumors that received adaptive immunotherapy using monocyte/macrophage therapy. Monocyte-mediated immunotherapy is performed using techniques well known and used in the art (Andreesen et al., 1998; Lesimple et al., 1998; Williams et al., 1999a, Williams et al., 1999b and Williams et al., 1999c)

It is contemplated that the antibodies bind TREM-1 splice variant resulting in a reduction of TREM-1 splice variant and an increase in TREM-1 levels resulting in an increase in inflammation and an augmentation of the immune response. This increase in inflammation is envisioned to increase the efficiency of the immunotherapy.

In addition to TREM-1 splice variant antibodies or antagonists can be administered, for example, but not limited to, TREM-1 splice variant antisense RNA.

Example 17

Modulation of Immune Mediated Graft Rejection

It is contemplated that the up-modulation of TREM-1sv production or the administration of TREM1-sv protein or derivatives is capable of decreasing the acute and chronic immunoreactions involved in graft rejection. This includes both solid organ and bone marrow transplantation.

Example 18

Modulation of Immune Reactions in Malignant and Non-malignant Histiocytic Disorders It is contemplated that the up-modulation of TREM-1sv or administration of TREM-1 or TREM1-sv protein or derivatives is capable of decreasing the release of inflammatory mediators and reducing the cardiovascular effects and tissue destruction seen in both malignant and non-malignant histiocytic disease such as: Langerhan Cell Histocytosis a.k.a. LCH, Hemophagocytic Lymphohistiocytosis a.k.a HLH, and Viral Associated Hemophagocytic Syndromes a.k.a. VAHS.

All patents and publications mentioned in the specification are indicative of the level of those skilled in the art to which the invention pertains. All patents and publications are herein incorporated by reference to the same extent as if each individual publication was specifically and individually indicated to be incorporated by reference.

REFERENCES

Altschul, S. F., Madden, T. L., Schäffer, A. A., Zhang, J., Zhang, Z., Miller, W., Lipman, D. J. *Nucl. Acids Res.* 25:3389-3402, 1997.

Andreesen R, Hennemann B, Krause S W. *J Leukocyte Biol* 64: 419-426, 1998

Aruffo et al., EMBO J. 6: 3313, 1987.

Bakker, A. B. H., Baker, E., Sutherland, G. R., Phillips, J. H., Lanier, L. L. *Proc. Natl. Acad. Sci. U.S.A.* 96:9792-9796, 1999.

Bangham et al., *J Mol. Biol.*, 13:238-252, 1965.

Barany G, Merrifield R B. *Anal Biochem.* 95(1):160-70, 1979.

Bartel, P. L. and S. Fields In: THE YEAST TWO-HYBRID SYSTEM. Oxford University Press, 1997.

Bellón, T., de Heredia, A. B., Llano, M., Minguela, A., Rodriguez, A., López-Botet, M., Aparicio, P. *J. Immunol.* 162, 3996-4002, 1999.

Berberian et al., *Science,* 261:1588-1591, 1993.

Bird et al., *Science*. Oct 21;242(4877):423-6, 1988.

Bouchon, A., Dietrich, J., Colonna, M. *J. Immunol.* 164: 4991-4995, 2000.

Campbell, In: Monoclonal Antibody Technology, Laboratory Techniques in Biochemistry and Molecular Biology, Vol. 13, Burden and Von Knippenberg, Eds. pp. 75-83, Amsterdam, Elseview, 1984.

Campbell, K. S., Colonna, M. *Int. J Biochem. Cell Biol.* 31:631-636, 1999.

Capaldi et al., *Biochem. Biophys. Res. Comm.,* 76:425, 1977.

Cleary et al., *Trends Microbiol.,* 4:131-136, 1994.

Coligan et al., Current Protocols in Immunology 1: Chapter 5 (1991).

Cook et al., *Cell*, 27:487-496, 1981.
Davis et al., BASIC METHODS IN MOLECULAR BIOLOGY, (1986).
DePalma, R. L., Krummel, T. M., Durham, L. A., et al., *Matrix*, 9:224-231, 1989.
Diatchenko, L., Lau, Y .F., Campbell, A. P., Chenchik, A., Moqadam, F., Huang, B., Lukyanov, S., Lukyanov, K., Gurskaya, N., Sverdlov, E. D., Siebert, P. D. *Proc. Natl. Acad. Sci. U.S.A* 93:025-6030, 1996.
Dietrich, J., Cella, M., Seiffert, M., Buhring, H. J., Colonna, M. *J Immunol* 164:9-12, 2000.
Dostal, G. H., and Gamelli, R. L.: *Surg. Gynecol Obstet.*, 176:299-306, 1993. DRUG CARRIERS IN BIOLOGY AND MEDICINE, G. Gregoriadis ed. (1979) pp. 287-341.
Eissa et al., *J Biol. Chem.* 271:27184-27187, 1996.
Fashena et al., *Methods Enzymol.* 328:14-26, 2000.
Forster and Symons, *Cell,* 49:211-220, 1987.
Gefter et al., *Somatic Cell Genet.* 3:231-236, 1977.
Gerlach et al., *Nature,* 328:802-805, 1987.
Gingras, M. C., Margolin, *J. Experimental Hematology* 28, 65-76, 2000.
Goding, In: Monoclonal Antibodies: Principles and Practice, 2d ed., Orlando, Fla., Academic Press, 60-61, 65-66, 71-74, 1986.
Gregoriadis and Davis, *Biochem Biophys Res Commun.,* 89(4):1287-1293, 1979
Gurskaya, N. G., et al., *Anal. Biochem.* 240:90-97, 1996.
Harlow and Lane, In: Antibodies: A laboratory Manual, Cold Spring Harbor Laboratories, Cold Spring Harbor, N.Y., 1988.
Hu et al., *Methods.* 20(1):80-94, 2000.
James et al., *Genetics.* 144(4):1425-36, 1996.
Johannesson et al., *J. Med. Chem.* 42:601-608, 1999.
Johnson et al., In: Biotechnology and Pharmacy, Pezzuto et al., eds., Chapman and Hall, New York, 1993.
Joyce *Nature,* 338:217-244, 1989.
Kaneda et al., *J Biol Chem.,* 264(21):12126-12129, 1989.
Kang et al., *Science,* 240:1034-1036, 1988.
Kato et al., *J Biol Chem.,* 266(6):3361-3364, 1991.
Kim and Cook, *Proc. Natl Acad. USA,* 84:8788-8792, 1987.
Kohler and Milstein, *Eur. J. Immunol.,* 6:511-519, 1976.
Kohler and Milstein, *Nature,* 256:495-497, 1975.
Kohler et al., *J Immunol Methods* 122(2):227-34, 1989.
Kreier et al., Infection, Resistance and Immunity, Harper and Row, New York, 1991.
Lamers, M. B. A. C., Lamont A. G., Williams, D. H. *Biochim Biophys. Acta* 1399:209-212, 1998.
Lanier, L. L., *Annu. Rev. Immunol.* 16:359, 1998.
Lanier, L. L., Corliss, B. C., Wu, J., Leong, C., Phillips, J. H. *Nature (London)* 391:703-707, 1998.
Lanier, L. L., Corliss, B. C., Wu, J., Phillips, J. H. *Immunity* 8:693-701, 1998.
Lenert et al., *Science,* 248:1639-1643, 1990.
Lesimple T, Moisan A, Toujas L. *Res Immunol* 149: 663-671, 1998
Mast, B. A., Diegelmann, R. F., Krummel, T. M., and Cohen, I. K.: *Surg. Gynecol. Obstet.,* 174:441-451, 1992.
Mast, B. A., Diegelmann, R. F., Krummel, T. M., and Cohen, I. K.: *Matrix,* 13:441-446, 1993.
Mast, B. A., Flood, L. C., Haynes, J. H., et al: *Matrix,* 11:63-68, 1991.
Merrifield B. *Science.* 232:341-7, 1986.
Michel and Westhof, *J.Mol.Biol,* 216:585-610, 1990.
Mount, S. M. *Nucl Acids Res.* 10:459-472, 1982.
Nicolau et al., *Methods Enzymol.,* 149:157-176, 1987.
Plougastel, B., Jones, T., Trowsdale, *J. Immunogenetics* 44:286-291, 1996.
Plougastel, B., Trowsdale, J. *Eur. J Immunol* 27:2835-2839, 1997.
Pugin, J., Ulevitch, R. J., and Tobias, P. S. *J.Exp.Med.* 178: 2193-2200, 1993.
Reinhold-Hurek and Shub, *Nature,* 357:173-176, 1992.
Remington's Pharmaceutical Sciences, 15th Edition, Chapter 61, pages 1035-1038 and 1570-1580.
Remington's Pharmaceutical Sciences, 16th Ed. Mack Publishing Company, 1980
Remington's Pharmaceutical Sciences, 18th Edition, Chapter 61, pages 1289-1329, 1990.
Rivett A J. *Biochem J.* 291 (Pt 1):1-10, 1993.
Rivett A J. *Enzyme Protein.* 47(4-6):210-9, 1993.
Rivett, A. *J. Biochem.* 291:1-10, 1993.
Roda-Navarro, P., Arce, I., Renedo, M., Montgomery, K., Kucherlapati, R., Fernandez-Ruiz, E. *Eur. J Immunol.* 30:568-576, 2000.
Sambrook et al., MOLECULAR CLONING: A LABORATORY MANUAL, 2nd Ed., Cold Spring Harbor Laboratory Press, Cold Spring Harbor, N.Y., 1989.
Sarver et al., *Science,* 247:1222-1225, 1990.
Sasso et al, *J Immunol.,* 142:2778-2783, 1989.
Scanlon et al., *Proc.Natl.Acad. USA,* 88:10591-10595, 1991.
Seed et al., *Proc. Natl. Acad. Sci. USA,* 84:3365, 1987.
Shorki et al., *J. Immunol.,* 146:936-940, 1991.
Silvermann et al., *J. Clin. Invest.,* 96:417-426, 1995.
Sundstrom, C., Nilsson, K. *Int. J. Cancer* 17:565-577, 1976.
Szoka and Papahadjopoulos, *Proc. Natl. Acad. Sci.,* 75:4194-4198, 1978.
Takahashi, K., Naito, M., Taketa, M. *Pathol. Int.* 46:473-485, 1996.
Tam et al., *Int J Pept Protein Res.* 21(1):57-65, 1983.
Tapping, R. I., Tobias, P. S. *Chem. Immunol.* 74:108-121, 2000.
Testa, U., Masciulli, R., Tritarelli, E., Pustorino, R., Mariani, G., Martucci, R., Barberi, T., Camagna, A., Valtieri, M., Peschle, C. *J. Immunol.* 150:2418-2430, 1993.
Tomasello, E., Olcese, L., Vé ly, F., Geourgeon, C., Bléry, M., Moqrich, A., Gautheret, D., Djabali, M., Mattei, M.G., Vivier, E. *J. Biol. Chem.,* 273:34115-34119, 1998.
Viriyakosol, S., Mathison, J. C., Tobias, P. S., Kirkland, T. N. *J. Biol. Chem.,* 275:3144-3149, 2000.
Vita et al., *Biopolymers* 47:93-100, 1998.
Weisshoff et al., *Eur. J Biochem.* 259:776-788, 1999.
Williams M A, Kelsey S M, Newland A C. *Eur J of Cancer* 35 (S3):S18-S22, 1999a.
Williams M A, Newland A C, Kelsey S M. In: Leukemia and Lymphoma 341:1-23, 1999b.
Williams M A, Rhoades C J, Newland A C, Kelsey S M. In: Leukemia and Lymphoma 341:207-230, 1999c.
Wong et al., *Gene,* 10:87-94, 1980.
Wong et al., *Mol Immunol.,* 32(5):379-87, 1995.
Wong et al., *Science,* 228: 810-815, 1985.
Yang et al., *Nucleic Acids Res.* 23(7):1152-6, 1995.

One of skill in the art readily appreciates that the present invention is well adapted to carry out the objectives and obtain the ends and advantages mentioned as well as those inherent therein. Proteins, peptide fragments, splice variants, vectors, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

What is claimed is:

1. A method of modulating an immune response including administering to an animal, in need thereof, a composition comprising a soluble polypeptide of SEQ ID NO: 2, or a fragment thereof, wherein said fragment consist of a portion of amino acid 1-136 of SEQ ID NO: 2, in an amount effective to modulate the levels of TREM-1 and /or ligand binding activity whereby the immune response is modulated in the animal.

2. The method of claim 1, wherein said polypeptide, or said fragment duplicate SEQ ID NO: 2, or a portion of amino acid 1-136 of SEQ ID NO: 2.

3. The method of claim 1 or 2, wherein said immune response is an inflammatory response.

4. The method of claim 1 or 2, wherein said polypeptide, or said fragment are admixed with a pharmaceutical carrier.

5. The method of claim 1 or 2, wherein the animal is suffering from a disease or condition is selected from the group consisting of organ transplant/rejection, bone marrow transplant/rejection, graft versus host disease, infectious disease, and an autoimmune disease.

6. The method of claim 5, wherein the disease or condition is an infectious disease and which is septic arthritis or septic shock.

7. The method of claim 5, wherein the disease or condition is an autoimmune disease and which is rheumatoid arthritis, lupus, multiple sclerosis and ulcer.

8. The method of claim 1, wherein the composition modulates LPS-induced cytokine production.

9. The method of claim 1 or 2, wherein the animal is a human.

* * * * *